United States Patent
Koch et al.

(10) Patent No.: US 10,143,524 B2
(45) Date of Patent: Dec. 4, 2018

(54) METHODS AND SYSTEMS FOR COUPLING A SURGICAL TOOL TO A TOOL DRIVER OF A ROBOTIC SURGICAL SYSTEM

(71) Applicant: Ethicon LLC, Guaynabo, PR (US)

(72) Inventors: Robert L. Koch, Cincinnati, OH (US); Jeffery Kirk, Liberty Township, OH (US); Andrew Beckman, Cincinnati, OH (US); Jeffrey S. Swayze, Hamilton, OH (US); Mark D. Overmyer, Cincinnati, OH (US); Eric W. Thompson, Pleasant Plain, OH (US); Kenneth Miller, Aptos, CA (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/381,453

(22) Filed: Dec. 16, 2016

(65) Prior Publication Data
US 2018/0168744 A1    Jun. 21, 2018

(51) Int. Cl.
*G05B 19/19*    (2006.01)
*A61B 34/30*    (2016.01)
(Continued)

(52) U.S. Cl.
CPC ........ *A61B 34/30* (2016.02); *A61B 17/00234* (2013.01); *A61B 46/17* (2016.02);
(Continued)

(58) Field of Classification Search
CPC ..................................................... A61B 34/30
(Continued)

(56) References Cited

U.S. PATENT DOCUMENTS 7,843,158 B2 * 11/2010 Prisco .................... A61B 34/71
                                                              318/566
8,114,345 B2    2/2012 Dlugos, Jr. et al.
(Continued)

FOREIGN PATENT DOCUMENTS

WO    WO-2011037394 A2    3/2011
WO    WO-2014151621 A1    9/2014
(Continued)

OTHER PUBLICATIONS

U.S. Appl. No. 15/200,283 entitled "Methods, Systems, and Devices for Initializing a Surgical Tool" filed Jul. 1, 2016.
(Continued)

*Primary Examiner* — David S Luo
(74) *Attorney, Agent, or Firm* — Mintz Levin/EES

(57) ABSTRACT

Systems and methods are provided for coupling a robotic surgical tool with a tool driver of a robotic surgical system via a sterile barrier disposed between the tool and the driver. The tool has an elongate shaft and an end effector coupled thereto, as well as a mating interface member having a plurality of independently movable portions and a plurality of coupling features disposed about a perimeter of an outer wall of the mating interface member. The coupling features are configured to reversibly engage with a proximal end of a corresponding actuation member from a plurality of actuation members of the tool driver. The coupling features reversibly engage with the proximal ends of the actuation members so as to allow the actuation members to move in proximal and distal directions independently from one another to thereby control operation of the end effector.

16 Claims, 33 Drawing Sheets

(51) Int. Cl.
*A61B 17/00* (2006.01)
*A61B 46/17* (2016.01)

(52) U.S. Cl.
CPC .............. *A61B 2017/00477* (2013.01); *A61B 2034/302* (2016.02)

(58) Field of Classification Search
USPC .................... 318/568.11, 568.1, 567, 560
See application file for complete search history.

(56) References Cited

U.S. PATENT DOCUMENTS

| | | | |
|---|---|---|---|
| 8,831,782 B2 | 9/2014 | Itkowitz | |
| 9,345,387 B2 * | 5/2016 | Larkin | A61B 1/00087 |
| 2015/0150638 A1 | 6/2015 | Lohmeier et al. | |
| 2015/0173840 A1 | 6/2015 | Lohmeier | |
| 2015/0216605 A1 | 8/2015 | Baldwin | |

FOREIGN PATENT DOCUMENTS

| | | |
|---|---|---|
| WO | WO-2014151952 A1 | 9/2014 |
| WO | WO-2015175200 A1 | 11/2015 |
| WO | WO-2016057989 A2 | 4/2016 |
| WO | WO-2016183054 A1 | 11/2016 |
| WO | WO-2017015599 A1 | 1/2017 |

OTHER PUBLICATIONS

U.S. Appl. No. 15/237,648 entitled "Methods, Systems, and Devices for Causing End Effector Motion With a Robotic Surgical System" filed Aug. 16, 2016.

International Search Report and Written Opinion for Intl. App. No. PCT/182017/057458 dated Feb. 27, 2018.

International Search Report and Written Opinion for Intl. App. No. PCT/182017/057459 dated Mar. 13, 2018.

* cited by examiner

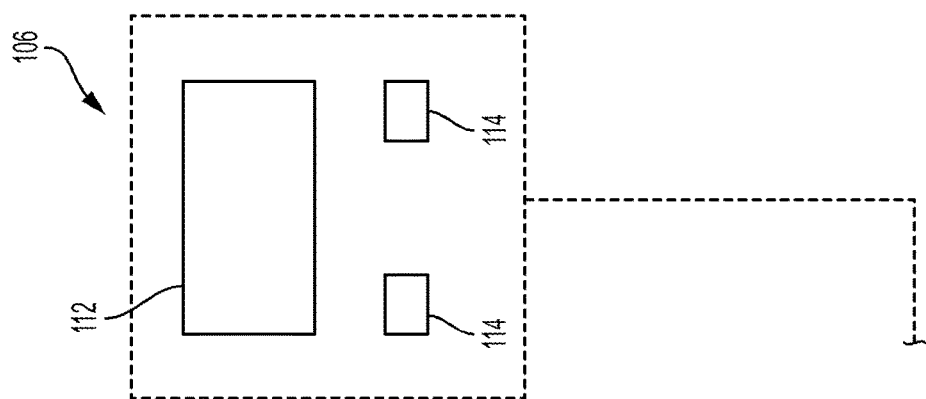
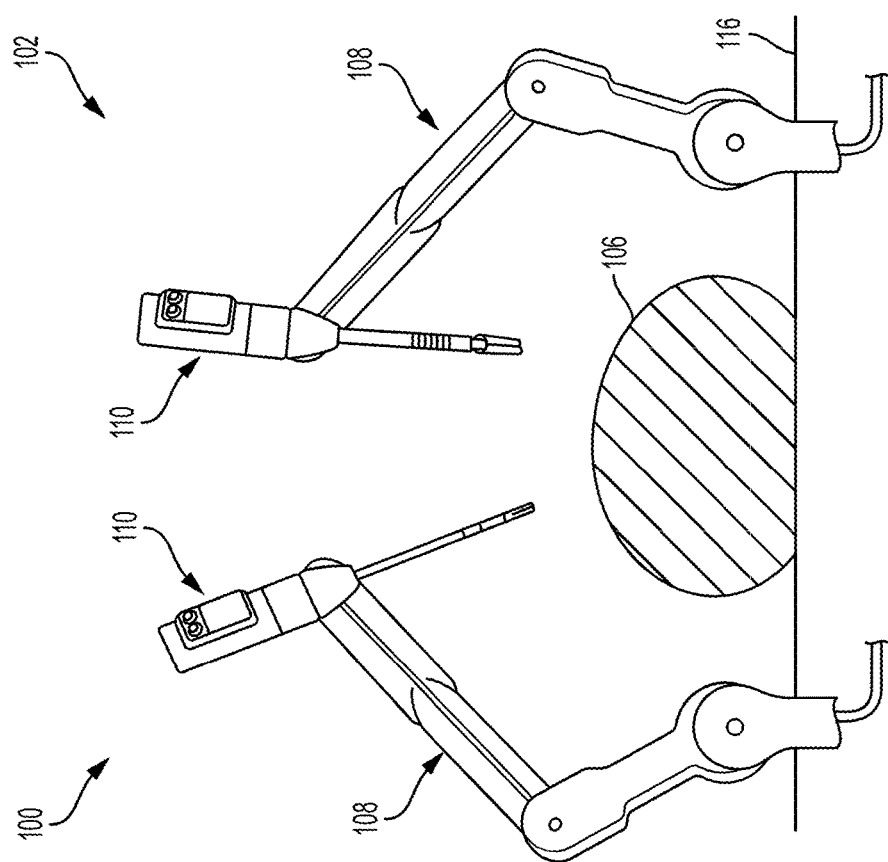
FIG. 2

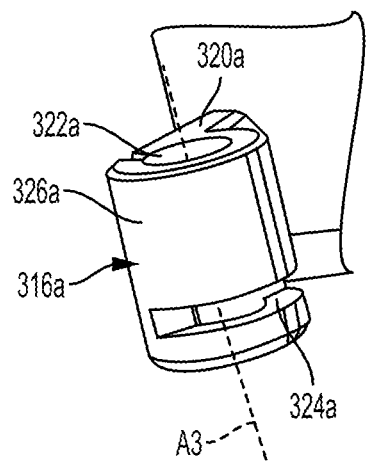
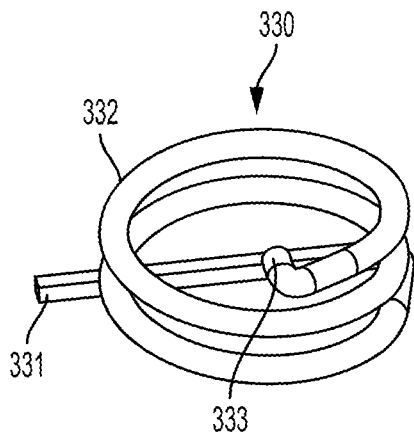
FIG. 10
FIG. 11
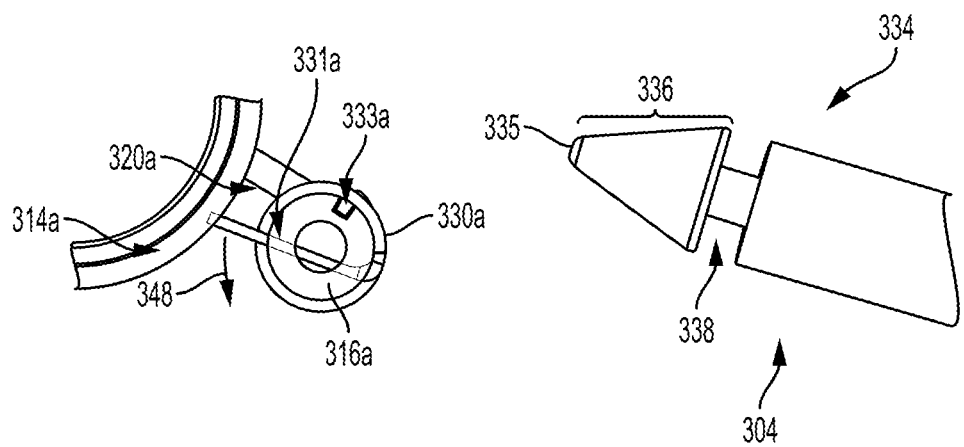
FIG. 12
FIG. 13

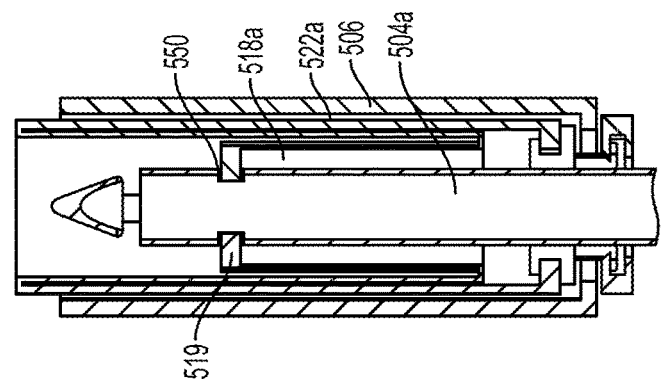
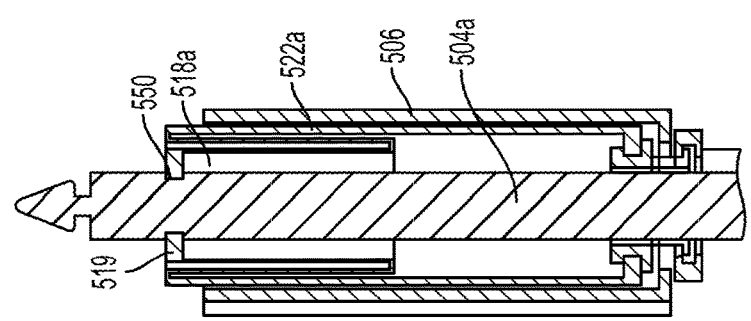
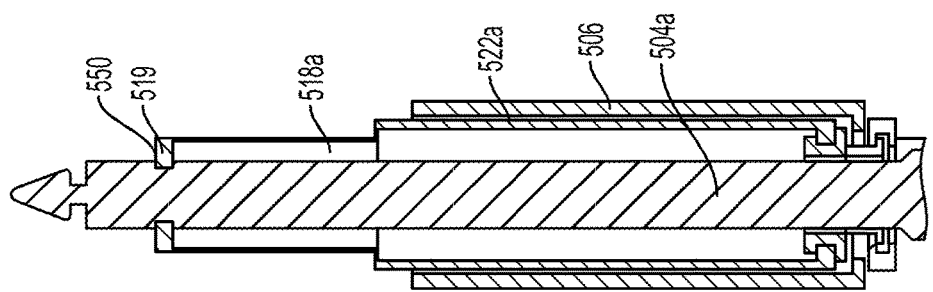
FIG. 35C
FIG. 35B
FIG. 35A

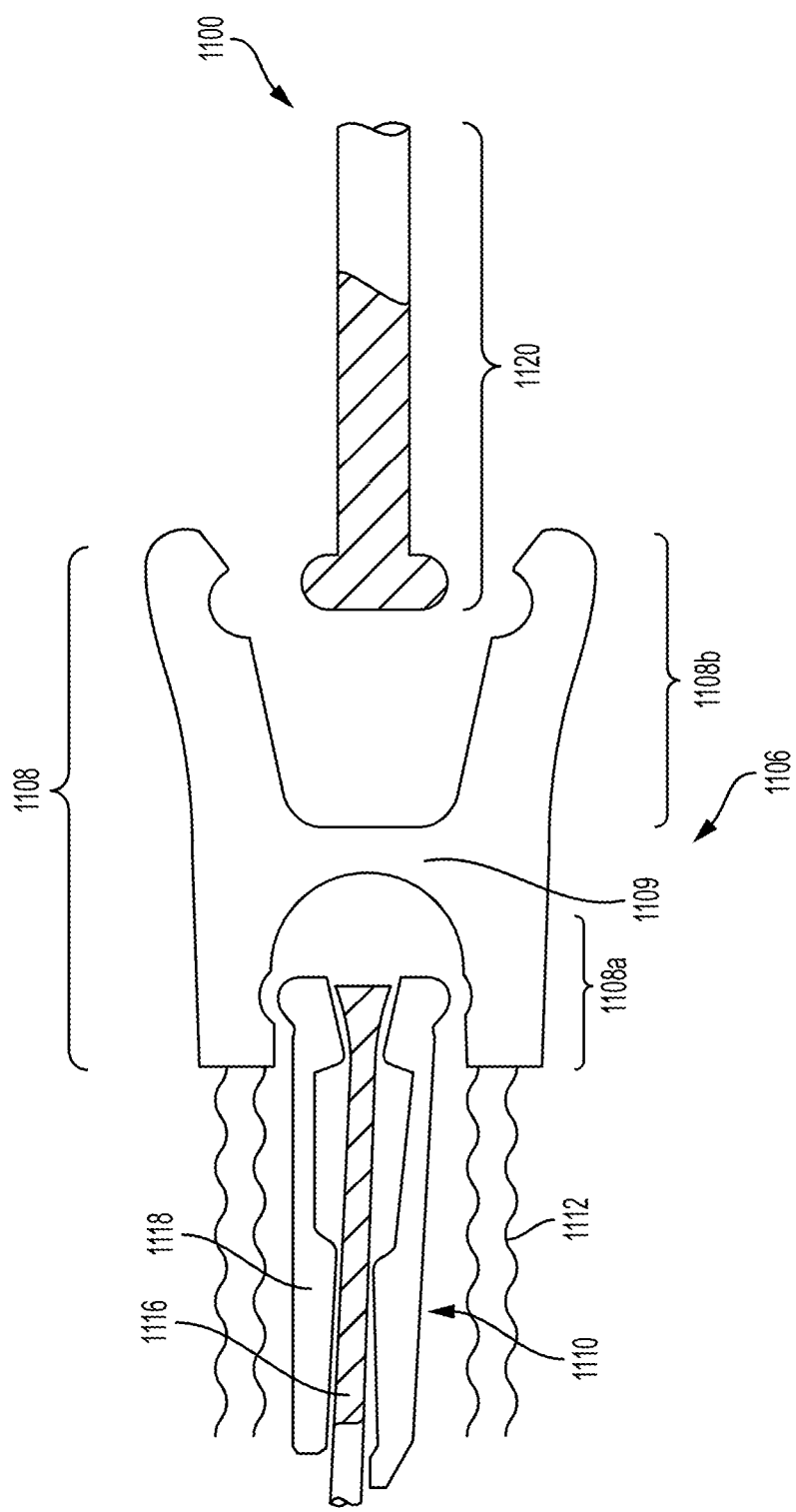

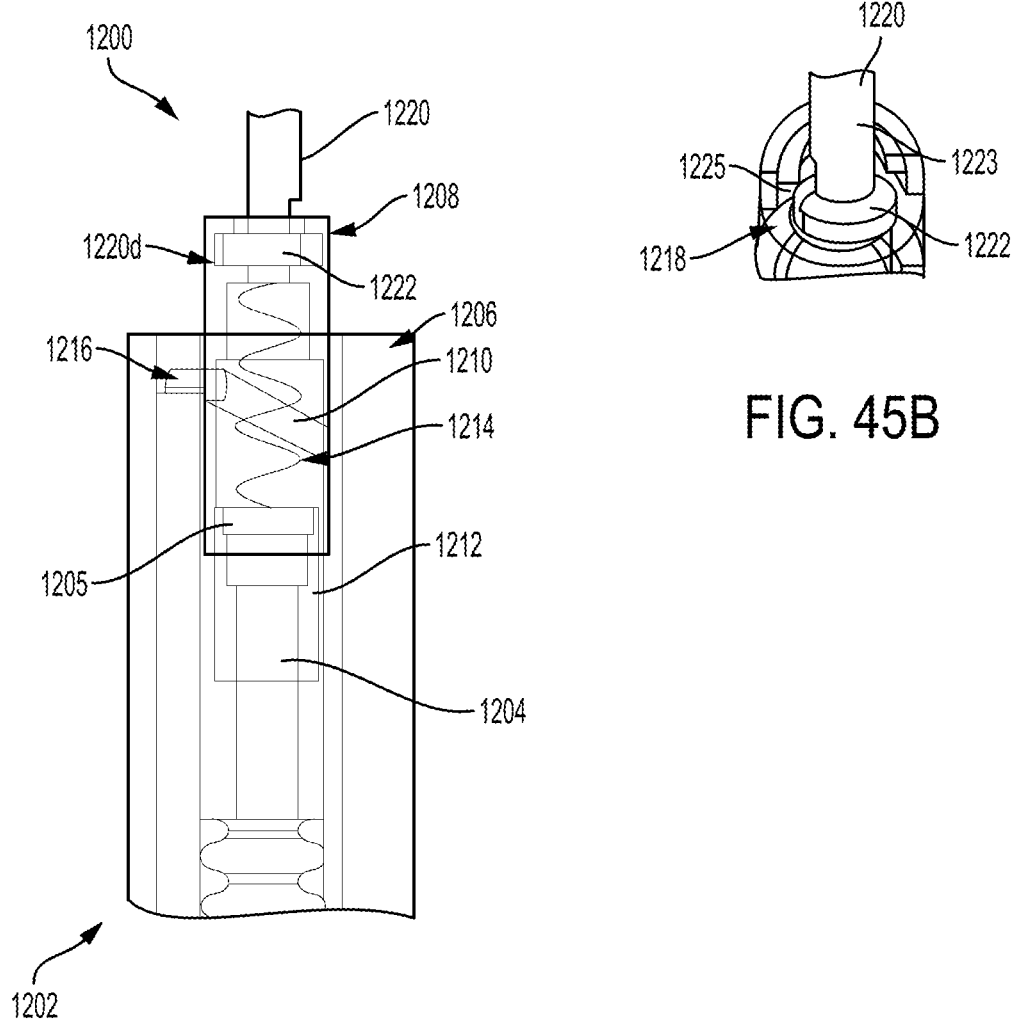

METHODS AND SYSTEMS FOR COUPLING A SURGICAL TOOL TO A TOOL DRIVER OF A ROBOTIC SURGICAL SYSTEM

FIELD

The present disclosure relates to various methods and systems for coupling a surgical tool to a tool driver of a robotic surgical system.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems including robotic arms, tool drivers coupled to the arms, and surgical tools mountable on the tool driver have been developed to assist in MIS procedures. However, there remains a need for improved methods, systems, and devices for operably coupling a surgical tool to a tool driver.

SUMMARY

In general, methods, systems, and devices for coupling a surgical tool to a tool driver of a robotic surgical system are provided.

In one aspect, a robotic surgical tool is provided that in some embodiments includes a housing comprising a mating interface member having a plurality of independently movable portions, an elongate shaft extending distally from the housing, an end effector coupled to a distal end of the elongate shaft, and a plurality of coupling features disposed about a perimeter of an outer wall of the mating interface member. Each of the plurality of coupling features is coupled to a movable portion and is configured to reversibly engage with a proximal end of a corresponding actuation member from a plurality of actuation members of a tool driver. The coupling features are configured to reversibly engage with the proximal ends of the actuation members so as to allow the actuation members to move in proximal and distal directions independently from one another to thereby control operation of the end effector.

The robotic surgical tool can vary in any of various ways. For example, it can further include a sterile barrier configured to be disposed between the surgical tool and the tool driver so as to define a sterile side at which the surgical tool is disposed and a non-sterile side at which a portion of the tool driver is disposed. The sterile barrier can encompass the coupling features engaged with the proximal ends of the actuation members.

As another example, each coupling feature can have an opening extending longitudinally therethrough that is configured to receive at least a portion of the proximal end of the actuation member. Each coupling feature can have an inner channel, an annular groove extending around at least a portion of an outer wall of the coupling feature, and a spring disposed around the outer wall and configured to engage a circumferential groove in the proximal end of the actuation member exposed through the annular groove when the proximal end is received within the inner channel of the coupling feature.

The surgical tool can also vary in many different ways. For example, in some embodiments, the surgical tool includes a movable disengagement member configured to cause all of the plurality of actuation members to simultaneously disengage from the coupling features. The disengagement member can be a generally cylindrical member having an open-ended passage extending therethrough and comprising first and second opposed ends connected by a plurality of longitudinal struts. The disengagement member can be disposed around the mating interface member that extends through the open-ended passage. The disengagement member can be configured to be rotated about its longitudinal axis so as to cause each longitudinal strut to move and to thereby disengage a respective spring from the circumferential groove in the proximal end.

In some embodiments, each coupling feature of the plurality of coupling features disposed about the perimeter of the outer wall of the mating interface member can be coupled to the proximal end of the actuation member via a sterile barrier coupler from a plurality of sterile barrier couplers, the sterile barrier coupler having a proximal portion configured to engage the coupling feature and a distal portion configured to engage the proximal end of the actuation member. The proximal portion of the sterile barrier coupler can have a first recess configured to engage the coupling feature, and the distal portion of the sterile barrier coupler can have a second recess having a shape complementary to a shape of the proximal end of the actuation member.

In some embodiments, the sterile barrier includes a removable coupling member configured to removably engage with the sterile barrier couplers and configured to be operated to simultaneously reversibly mate the sterile barrier couplers with the proximal ends of the actuation members. The removable coupling member can include an actuator, a body, and a plurality of coupling sleeves extending from the body and configured to reversibly engage with the sterile barrier couplers. The actuator can be configured to be rotated in a first direction to cause the sleeves to rotate and thereby cause the sterile barrier couplers engaged with the sleeves to engage with the proximal ends of the actuation members, and in a second, opposite direction to cause the sleeves to rotate and thereby cause the sterile barrier couplers engaged with the sleeves to disengage from the proximal ends of the actuation members.

In some embodiments, the robotic surgical tool includes a rotatable portion disposed proximally of the elongate shaft and configured to be axially rotated between a first position and a second position to thereby cause all of the coupling features to simultaneously engage with and simultaneously disengage from corresponding proximal portions of the sterile barrier couplers.

In some embodiments, the distal portion of each of the sterile barrier couplers has a bellows extending distally therefrom, a proximal portion of the actuation member has its proximal end engaged with the distal portion of the sterile barrier coupler extends through the bellows, and a distal end of the bellows is disposed at a distal end of the sterile barrier. Each of the bellows can allow the proximal portion of the actuation member extending therethrough to move therewithin in proximal and distal directions such that the actuation members move independently from one another.

The actuation members of the tool driver can be actuated in any of various ways. For example, each actuation member can be operably coupled with at least one motor disposed in the tool driver and configured to control movement of the actuation member.

In another aspect, a sterile barrier is provided that is configured to be disposed between a tool driver and a surgical tool of a robotic surgical system to define a sterile side at which the surgical tool is disposed and a non-sterile side at which a portion of the tool driver is disposed. In some embodiments, the sterile barrier includes a housing configured to accommodate proximal portions of a plurality of actuation members of a tool driver when the sterile barrier is coupled to the tool driver such that the actuation members extend proximally from the tool driver and at least partially through the sterile barrier, and a plurality of substantially cylindrical, longitudinally expandable bellows disposed at least partially within the housing and each configured to encompass and mate with the proximal portion of a corresponding one of the plurality of actuation members.

The sterile barrier tool can vary in any of various ways. For example, the bellows can be formed from an elastomeric material. As another example, each of the bellows can include at least outer and inner portions, the inner portion being disposed at least partially within the outer portion and being configured to move longitudinally relative to the outer portion. In some embodiments, the inner portion of the bellows has a mating feature disposed on a proximal end thereof that is configured to reversibly mate with a complementary mating feature formed on the actuation member.

In some embodiments, a distal end of the outer portion of the bellows is coupled to a distal end of the housing of the sterile barrier. The outer portion of the bellows can be coupled to the distal end of the sterile barrier via an insert feature extending through a distal end of the bellows and through the distal end of the sterile barrier, and via a snap ring disposed over a portion of the insert feature extending from the distal end of the sterile barrier.

The housing of the sterile barrier can vary in many different ways. For example, at least a portion of the housing can be substantially rigid. In some embodiments, the housing has a plurality of longitudinal, generally cylindrical enclosure portions each configured to receive therethrough the proximal portion of the corresponding actuation member. In some embodiments, the sterile barrier further includes at least one flexible fabric attached to the housing.

The actuation members can be configured to move in proximal and distal directions independently from one another.

In other aspects, a robotic surgical system is provided that in some embodiments includes a plurality of sterile barrier couplers of a sterile barrier. The sterile barrier couplers can be configured to reversibly couple a surgical tool and a tool driver of the robotic surgical system via the sterile barrier, and each of the sterile barrier couplers can have a first portion configured to engage with a proximal end of a corresponding one of a plurality of tool driver actuation members of the tool driver, and a second portion configured to engage with a corresponding one of a plurality of tool actuation members of the surgical tool.

The robotic surgical system can vary in any of various ways. For example, it can include at least one bellows coupled to and extending distally from each of the sterile barrier couplers. As another example, the first portion of the sterile barrier coupler can include a first recess configured to receive therein the proximal end of the corresponding actuation member, wherein a configuration of the recess is complementary to a configuration of the proximal end. The second portion of the sterile barrier coupler can include a second recess configured to receive therein a distal end of the tool actuation member.

In some embodiments, the sterile barrier coupler can include a pin member having first and second grooves configured to receive therein a coil disposed at a distal end of the tool actuation member.

In some embodiments, the robotic surgical system further includes a retainer member having a body and a plurality of retaining features each configured to engage a recess in the proximal portion of a corresponding one of the plurality of sterile barrier couplers.

In some embodiments, the recess in the second portions of each of the sterile barrier couplers is configured to receive therein a distal end of the tool actuation member after the retainer member is separated from the sterile barrier couplers.

In some embodiments, the sterile barrier includes a curved path feature that causes each of the sterile barrier couplers to move therealong when the sterile barrier coupler is moved distally during distal advancement of the surgical tool through the sterile barrier when a distal end of a tool driver actuation member is engaged with the sterile barrier coupler.

BRIEF DESCRIPTION OF THE DRAWINGS

The present disclosure will be more fully understood from the following detailed description taken in conjunction with the accompanying drawings, in which:

FIG. 2 is a perspective view of one embodiment of a surgical robotic system that includes a patient-side portion and a user-side portion;

FIG. 10 is another perspective view of a coupling feature of the surgical tool, with the coupling feature shown without a spring;

FIG. 11 is a perspective view of the spring of FIG. 9;

FIG. 12 is a top view of a coupling feature of the surgical tool, with the coupling feature being shown with a spring;

FIG. 13 is a perspective view of a proximal end of an actuation member of a tool driver;

FIG. 35A is a schematic, cross-sectional diagram illustrating the most proximal position of the actuation member of the tool driver of FIG. 30, the actuation member being movably coupled to the bellows of the sterile barrier;

FIG. 35B is a schematic, cross-sectional diagram illustrating the "home" position of the actuation member of FIG. 35A;

FIG. 35C is a schematic, cross-sectional diagram illustrating the most distal position of the actuation member of FIG. 35A;

FIG. 44 is a schematic cross-sectional view of one implementation of a clip member in accordance with the described techniques;

FIG. 45A is a cross-sectional view of another implementation of a sterile barrier coupler configured to couple an actuation member and a surgical tool to one another via a sterile barrier, showing the surgical tool being not coupled to the sterile barrier coupler;

FIG. 45B is an enlarged view of the sterile barrier coupler and a distal portion of a tool actuation member of the surgical tool of FIG. 45A;

DETAILED DESCRIPTION

Figure 1:
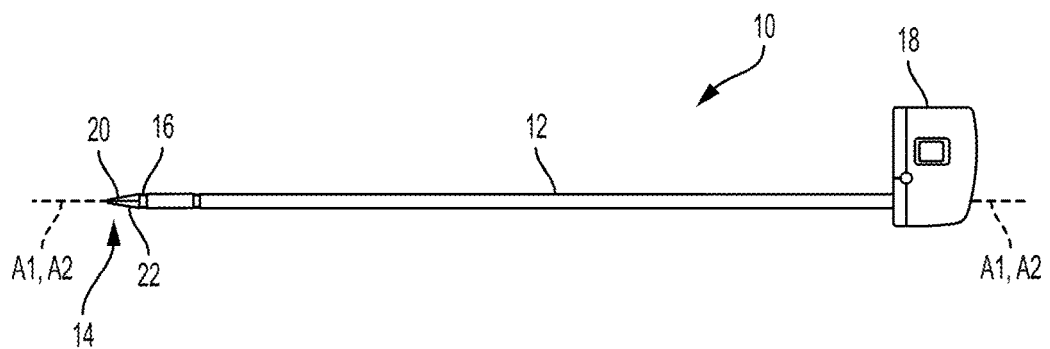
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In some implementations, a surgical tool and a tool driver of a robotic surgical system are coupled via a sterile barrier disposed between the tool and the tool driver so as to create a sterile side at which the tool is disposed and a non-sterile side at which a portion of the tool driver is disposed. The tool is removably coupled to the tool driver in a manner that allows operating the tool through the sterile barrier, without interfering with the integrity of the barrier and while allowing movement of tool driver's actuation members within the sterile barrier. The described techniques provide a straight-forward way of reversibly coupling the surgical tool with the tool driver through the sterile barrier.

FIG. 1 illustrates an example of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. It should be appreciated that the tool 10 and its components are shown by way of example only and that the described subject matter can be implemented in connection with a surgical tool having other configurations. For example, although the elongate shaft 12 is shown in FIG. 1 as disposed off-center with respect to the housing 18, in some implementations, the shaft 12 can be close to the center or centered with respect to the housing 18. Also, the configuration of the housing 18 in FIG. 1 is shown by way of example only. For example, a length of the housing 18, as measured along a side thereof parallel to a longitudinal axis A1 of the shaft, can be greater than the length shown in FIG. 1. In other words, the housing 18, shaft 12, and other components of the tool 10 are shown solely for the purpose of illustrating generally a surgical tool, and not to show any specific configuration of the surgical tool.

The end effector 14 is configured to move relative to the shaft 12 at the wrist 16, e.g., by pivoting at the wrist 16, to position the end effector 14 at a desired location relative to a surgical site during use of the tool 10. The housing 18 includes various components (e.g., gears and/or actuators) configured to control the operation of various features associated with the end effector 14 (e.g., any one or more of clamping, firing, rotation, articulation, energy delivery, etc.). In at least some embodiments, the shaft 12, and hence the end effector 14 coupled thereto, are configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, a stapler, forceps, a grasper, a needle driver, scissors, an electrocautery tool that applies energy, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have also any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This tray allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

The wrist 16 can have any of a variety of configurations. Exemplary embodiments of a wrist of a surgical tool and of effecting articulation at the wrist are described in International Patent Publication No. WO 2014/151952 entitled "Compact Robotic Wrist" filed on Mar. 13, 2014, International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., an X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

Figure 1A:
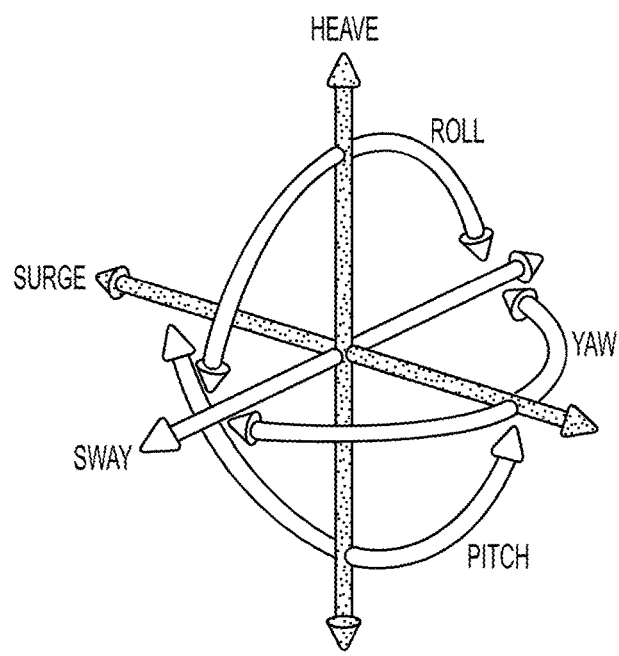
FIG. 1A is a graphical representation of terminology associated with six degrees of freedom.

FIG. 1A illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 1A, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The surgical tool 10 includes a plurality of flexible members (obscured in FIG. 1) configured to effect the movement of the end effector 14 relative to the shaft 12. The flexible members are operably coupled to the tool housing 18, extend along the shaft 12, extend through the wrist 16, and are operably coupled to the end effector 14. In an exemplary embodiment, the flexible members extend distally from the tool housing 18 along the shaft 12 within an inner lumen of the shaft 12. The flexible members can be selectively actuated to cause the end effector 14 to pivot at the wrist 16 relative to the shaft 12. The selective actuation of the flexible members can cause any one or more of the flexible members to move, e.g., translate longitudinally, to cause the articulation. The one or more of the flexible members that translate depend on the requested articulation, e.g., the appropriate one or more of the flexible members flex to cause the end effector 14 to yaw and/or pitch as requested. The actuation can be accomplished in any of a variety of ways, such as by actuating one or more actuating member operably coupled to the tool housing 18, as discussed further below. In general, the actuation applies tension to the one or more of the flexible members in a proximal direction to cause the one or more of the flexible members to translate and thereby cause the end effector 14 to articulate relative to the shaft 12. In other words, the actuation pulls the one or more of the flexible members proximally. Furthermore, as in some implementations described below, the actuation can also push the one or more of the flexible members distally. The flexible members can also be selectively actuated to open and close the jaws 20, 22, e.g., to move the end effector 14 between open and closed positions. When both of the jaws 20, 22 are configured to move to open and close the end effector 14, at least one of the flexible members can be operably coupled to one of the jaws 20 to move that jaw 20 and at least one other of the flexible members can be operably coupled to the other one of the jaws 22 to move that jaw 22. When only one of the jaws 20, 22 is configured to move to open and close the end effector 14, at least one of the flexible members can be operably coupled to that one of the jaws 20, 22 to move that one of the jaws 20, 22.

The plurality of flexible members can have any of a variety of configurations, for example cables, rods, wires, or twisted strings. The flexible members can be made from any of a variety of materials, such as a metal (e.g., Tungsten, stainless steel, etc.). Exemplary embodiments of flexible members of a surgical tool are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

The movement of the end effector 14 caused by movement of one or more of the flexible members includes movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1.

As mentioned above, the tool housing 18 is shown in FIG. 1 by way of example only and it can have any of a variety of configurations. In general, the tool housing 18 can include one or more actuation mechanisms at least partially disposed therein configured to cause movement of the plurality of flexible members and thereby cause movement of the end effector 14 about the wrist 16. The one or more actuation mechanisms can include, for example, one or more movement mechanisms operably coupled to the plurality of flexible members, such as pulley(s) configured to be moved to cause translation of the flexible members. The tool housing 18 is configured to be releasably attached to a robotic surgical system (also referred to herein as a "robot" or "surgical robot") so as to releasably attach the tool 10 to the robot. The tool housing 18 can be configured to releasably attach to a robot in any of a variety of ways, as will be appreciated by a person skilled in the art, such as by clamping thereto, clipping thereto, or slidably mating therewith. The one or more movement mechanisms are configured to be controlled by the robot, as will be appreciated by a person skilled in the art, such as by the robot including one or more motors operably coupled to one or more inputs of the tool housing 18 that are operably coupled to the one or more movement mechanisms. The robot includes a computer system that can receive user inputs and can control the motor(s) in response to the user inputs and hence control movement of the flexible members and consequently the end effector 14.

Exemplary embodiments of robotic surgical systems are described in U.S. Pat. No. 8,831,782 entitled "Patient-Side Surgeon Interface for a Teleoperated Surgical Instrument" filed Jul. 15, 2013, which is hereby incorporated by reference in its entirety, and in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014. Also, exemplary embodiments of a tool housing of a surgical tool including one or more actuation mechanisms and configured to releasably attach to a robotic surgical system are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

FIG. 2 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each tool assembly 110 during a surgical procedure.

The control system 114 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more parts of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

The patient-side portion 102 can have a variety of configurations. As illustrated in FIG. 2, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 2). Alternatively, the patient-side portion 102 can include a single assembly that includes one or more robotic arms 108 extending therefrom.

Figure 3:
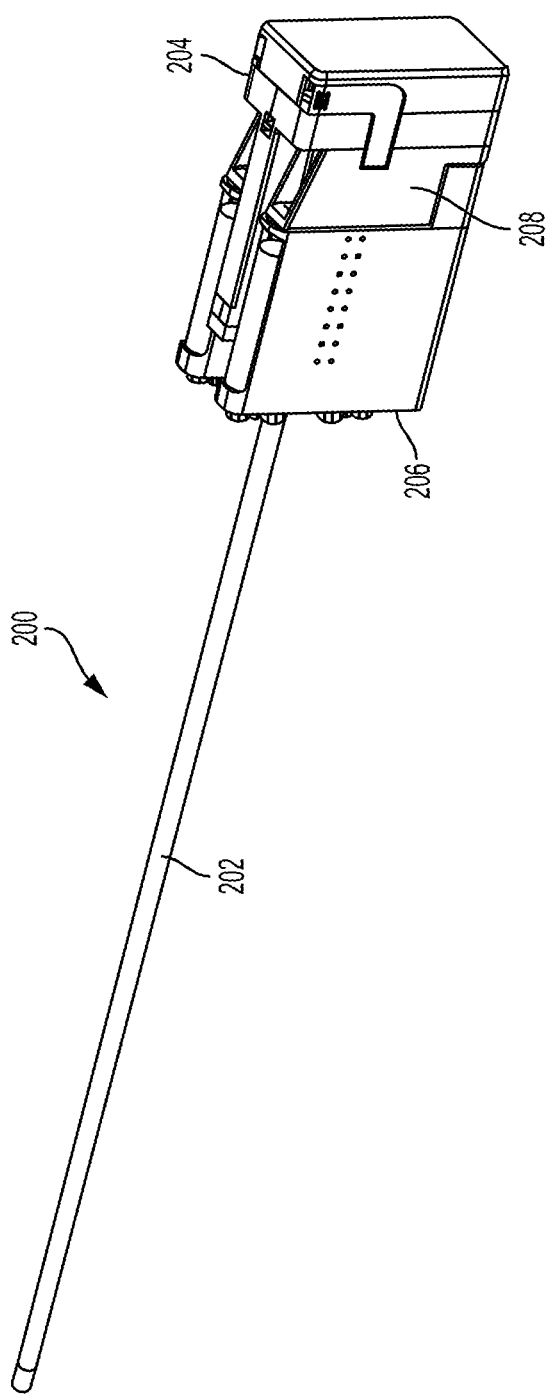
FIG. 3 is a perspective of a portion of another embodiment of a surgical tool coupled to one embodiment of a tool driver and sterile barrier of a robotic surgical system.
Figure 4:
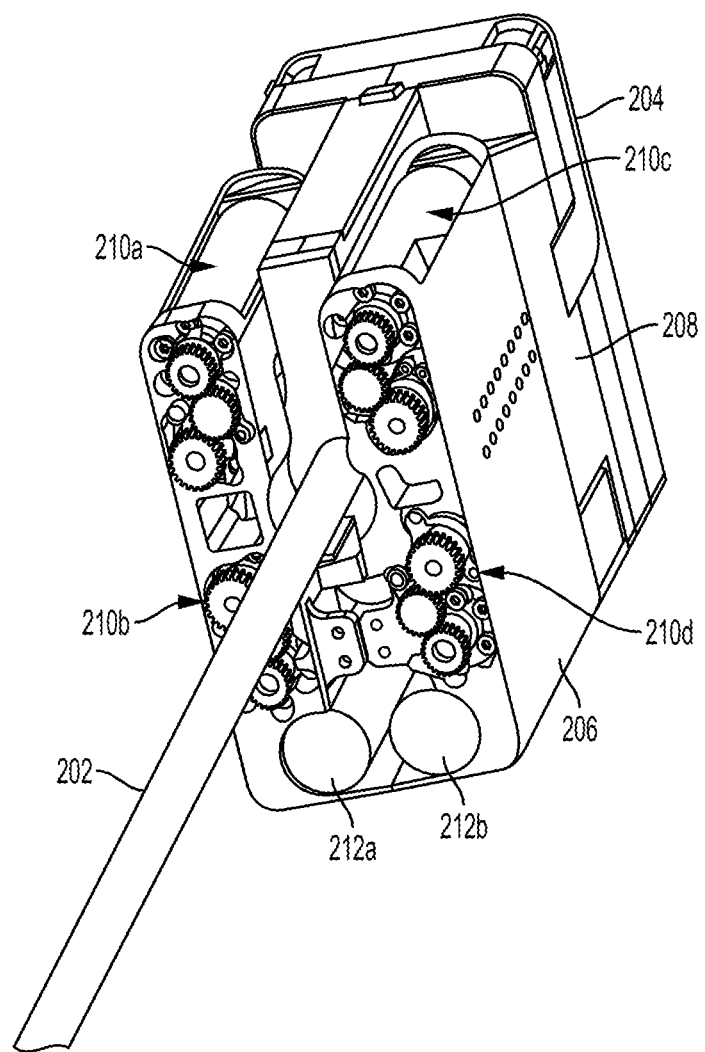
FIG. 4 is a perspective view of the tool driver, sterile barrier, and a proximal portion of the surgical tool of FIG. 3.

FIGS. 3 and 4 illustrate another embodiment of a surgical tool 200 that includes an elongate shaft 202, an end effector (not shown), a wrist (not shown) that couples the end effector to the shaft 202 at a distal end of the shaft 202, a tool housing 204 coupled to a proximal end of the shaft 202, and a plurality of flexible members (not shown). The surgical tool 200 can be configured and used generally similar to the tool 10 of FIG. 1, though the tool 200 can have other configurations of its components. Only a proximal portion of the tool 200 is shown in FIG. 3. This proximal portion of the tool 200 can be the proximal portion of the tool 10 of FIG. 1 or the proximal portion of another suitable tool, such as one of the surgical tools described below.

FIG. 3 shows the tool 200 releasably coupled to one embodiment of a robotic surgical system. The tool housing 204 is releasably coupled to a tool driver 206 of the robotic surgical system with the shaft 202 of the tool 200 extending distally from the tool housing 204 and the tool driver 206. Only a partial portion of the robotic surgical system is shown in FIGS. 3 and 4 for clarity of illustration.

The robotic surgical system also includes a sterile barrier 208 to which a sterile shroud or drape (not shown) can be attached for sterility purposes, as will be appreciated by a person skilled in the art. The placement of the sterile barrier 208 between the tool housing 204 and the tool driver 206 may ensure a sterile coupling point for the tool 200 and the robot and thereby permit removal the tool 200 from the robot to exchange with other surgical tools during the course of a surgery without compromising the sterile surgical field.

The tool driver 206 can have any of a variety of configurations, as will be appreciated by a person skilled in the art. The tool driver 206 includes one or more motors for controlling a variety of movements and actions associated with tools such as the tool 200 that can be releasably coupled to the tool driver 206, as will be appreciated by a person skilled in the art. In this illustrated embodiment, as shown in FIG. 4, the tool driver 206 includes six motors, four motors 210a, 210b, 210c, 210d for driving movement/action using activation features and one motor 212a, 212b for each of two rotary couplings of the tool driver 206 for driving movement/action through rotary motion. For example, each motor 210a, 210b, 210c, 210d, 212a, 212b can couple to and/or interact with an activation feature (e.g., gear) associated with the tool 200 for controlling one or more actions and movements that can be performed by the tool 200 such as movement of the tool's flexible members relative to the shaft 202, articulation of the tool's end effector, rotation of the shaft 202 about its longitudinal axis, etc. The motors 210a, 210b, 210c, 210d, 212a, 212b are accessible through a proximal end of the sterile barrier 208, and the tool housing 204 of the tool 200 is configured to mount on the proximal end of the sterile barrier 208 to couple to the sterile barrier 208 and the tool driver 206. Exemplary embodiments of motors and movements and actions motors can drive are described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014.

In the examples of FIGS. 3 and 4, each of the four motors 210a, 210b, 210c, 210d is operably coupled to one of the tool's flexible members via a corresponding coupling feature disposed within the tool housing 204. The movement of the flexible members (e.g., pulling and pushing thereof in proximal and distal directions) can thus be independently controlled by their associated one of the motors 210a, 210b, 210c, 210d. Rotary motion of the motors 210a, 210b, 210c, 210d can thus be configured to cause translational movement of the flexible members. One of the rotary couplings can be driven by the motor 212a to rotate the shaft 202. The tool housing 206 can includes a pulley system (not shown) operably coupled to the first rotary coupling to transfer the power of the motor 212a to the shaft 202 for rotation thereof. Rotary motion can thus be configured to cause rotational movement of the shaft 202.

The tool driver 206 includes a receiving channel (not shown) formed in a wall thereof for receiving a distal portion of the tool housing 204 and a proximal portion of the shaft 202 of the tool 200. In some embodiments, the tool housing 204 and shaft 202 can extend through an opening formed in the tool driver 206, or the tool 200 and the tool driver 206 can mate in various other ways. The sterile barrier 208 also includes a receiving channel (not shown) formed in a wall thereof for receiving a proximal portion of the tool driver 206 and the distal portion of the tool housing 204. A proximal end of the shaft 202 is located distal to the sterile barrier 208. In other words, the shaft 202 does not extend proximally far enough to reach the sterile barrier 208. The shaft 202 can thus be contained within the sterile surgical area.

The tool housing 204 can includes features configured to assist with releasably coupling the tool housing 204 to the tool driver 206, and hence for coupling the tool 200 to the robotic surgical system. For example, the tool housing 204 can include gears and/or actuators configured to be actuated by one or more of the motors 210a, 210b, 210c, 210d, 212a, 212b. The gears and/or actuators in the tool housing 204 can control the operation of various features associated with the tool's end effector (e.g., clamping, firing, rotation, articulation, energy delivery, forcing to an unarticulated position, etc.), as well as control the movement of the shaft 202 (e.g., rotation of the shaft). The shaft 202 can include actuators and connectors that are operatively coupled to the gears and/or actuators in the tool housing 204 and that extend along the shaft 202 to assist with controlling the actuation and/or movement of the end effector and/or the shaft 202.

As discussed above, in the described implementations, a surgical tool having an elongate shaft and an end effector coupled to a distal end of the shaft is configured to removably mate with a tool driver of a robotic surgical system. A sterile barrier is disposed between the surgical tool and the tool driver to prevent contamination of the robotic surgical system during a surgical procedure, such that the sterile environment of the tool is not compromised.

Furthermore, in some embodiments, devices, systems, and methods for coupling the tool to the tool driver are provided to allow not only push movements, but also pull of actuating members of the tool driver that actuate corresponding elements of the tool and the end effector, such as the flexible members described above that are configured to effect the movement of the tool's end effector relative to the tool's shaft. In particular, the tool driver's actuating members are configured to independently move proximally and distally a certain distance. The tool driver's actuating members perform push and pull linear movements at least partially within the sterile barrier disposed between the tool and the tool driver. The devices, systems, and methods described herein provide a way to reversibly couple the tool driver's actuating members to the surgical tool via a sterile barrier disposed between the tool driver and tool. In particular, techniques are provided for aligning and reversibly mating coupling features of the surgical tool to the actuating members of the tool driver.

Figures 5A, 5B:
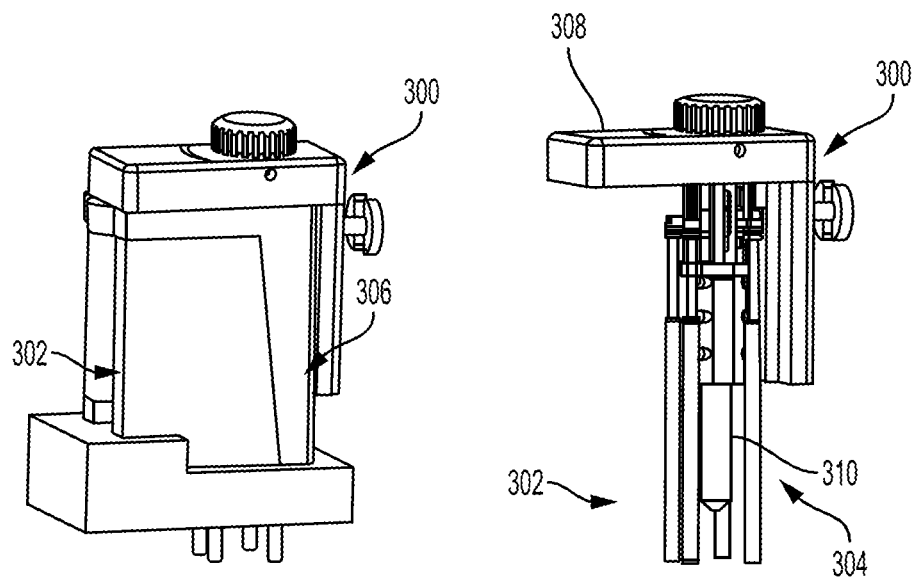
FIG. 5A is a perspective view of one implementation of a proximal portion of a surgical tool, a tool driver, and a sterile barrier.
FIG. 5B is another perspective view of the implementation of the proximal portion of the surgical tool and the tool driver of FIG. 5A.

FIGS. 5A-16B illustrate one embodiment of a surgical tool 300 configured to reversibly mate with a tool driver 302 of a robotic surgical system. The tool driver 302 has a plurality of actuation members 304a, 304b, 304c, 304d, which are discussed in more detail below. As shown in FIG. 5A, a sterile barrier 306 is disposed between the tool 300, a proximal portion of which is shown, and the tool driver 302. The sterile barrier 306 is shown separately in FIG. 6.

Figure 7:
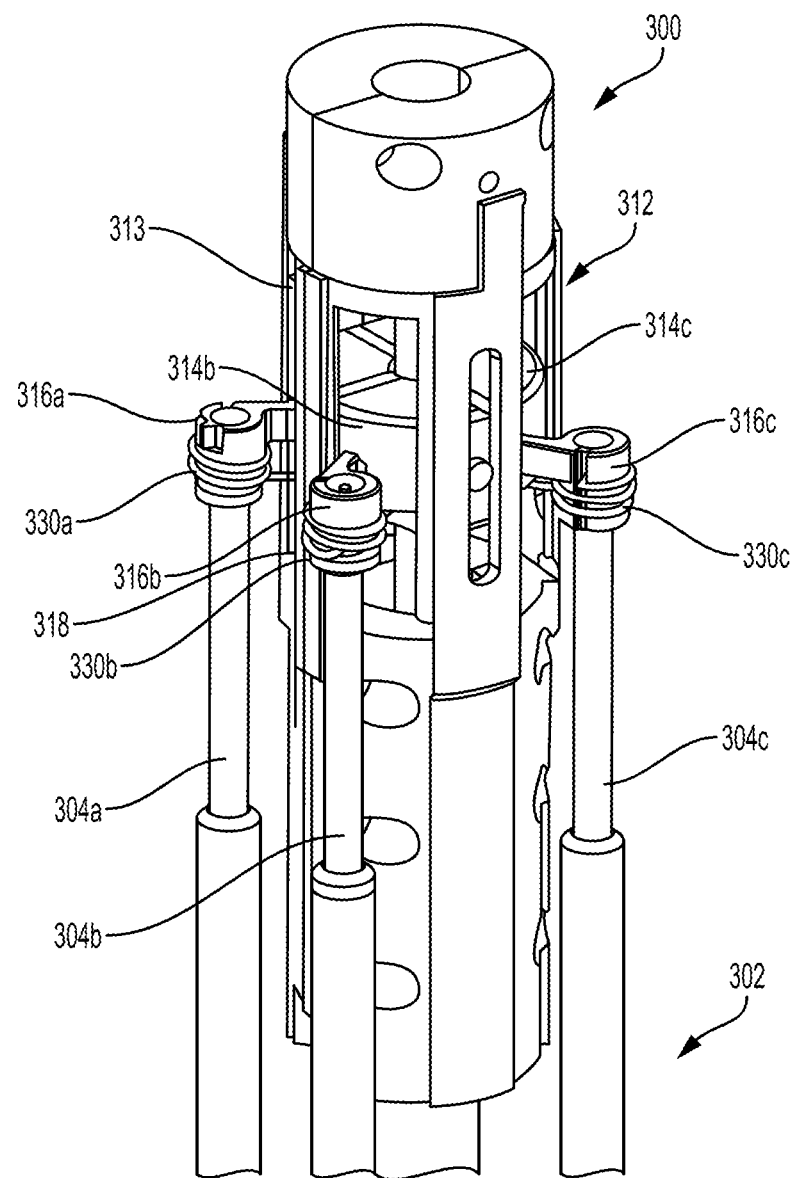
FIG. 7 is a perspective, partial view of the surgical tool and the tool driver's actuation members of FIG. 6.

The surgical tool 300 includes a housing 308 and an elongate shaft 310 extending distally from the housing 308. Only the proximal portion of the shaft 310 is shown in FIG. 5B for the clarity of description. As shown in FIG. 7, the surgical tool 300 includes a mating interface member 312 having features for releasably mating the tool 300 to the tool driver 302. The mating interface member 312 has a plurality of tool plungers or movable portions 314a, 314b, 314c, 314d (FIGS. 7 and 8), which are configured to move independently from one another. In the example illustrated, as shown in FIG. 7 illustrating a portion of the tool 300 and the actuation members 304a, 304b, 304c, 304d coupled therewith, the movable portions 314a, 314b, 314c, 314d are radially adjacent to one another and are disposed within a tool body 313 of the mating interface member 312. It should be appreciated that the mating interface member 312 includes other components that are not shown herein for clarity of description.

The surgical tool 300 also has a plurality of coupling features 316a, 316b, 316c, 316d disposed around a perimeter of an outer wall 318 of the mating interface member 312. The coupling features 316a, 316b, 316c, 316d (FIG. 8) are coupled to the mating interface member 312 such that each of the coupling features is attached to a corresponding one of the movable portions 314a, 314b, 314c, 314d. Thus, each of the coupling features is movable with respect to the tool body 313. The coupling features 316a, 316b, 316c, 316d are configured to reversibly engage with proximal ends of actuation members 304a, 304b, 304c, 304d of the tool driver 302. In this way, the tool driver's actuation members 304a, 304b, 304c, 304d cause the movable portions 314a, 314b, 314c, 314d to move independently from one another.

The coupling features 316a, 316b, 316c, 316d can have any of a variety of different configurations. In the example illustrated, as shown by way of example in FIGS. 9 and 10 for the coupling feature 316a, each of the coupling features is a substantially cylindrical element attached to a corresponding movable portion via an arm 320a, 320b, 320c, 320d. Each coupling feature has a substantially cylindrical inner channel 322a, 322b, 322c, 322d extending therethrough and configured to receive a proximal end of one of the actuation members 304a, 304b, 304c, 304d of the tool driver 302. As shown in FIG. 10 for the coupling feature 316a as a representative coupling feature of the coupling features 316a, 316b, 316c, 316d, each coupling feature also has an annular groove or slot 324a formed on an outer wall 326a of the coupling feature and extending through at least a portion of the outer wall 326a. The annular slot 324 is in communication with the channel 322a, as shown in FIG. 10. A longitudinal slot 328a extending through the entire height (or length) of the coupling feature 316a along a longitudinal axis A3 thereof is formed in the area of the outer wall 326a of the coupling feature 316a that is not occupied by the annular slot 324a.

It should be appreciated that one or more of the coupling features 316a, 316b, 316c, 316d can have any other features. For example, the outer wall of a coupling feature can have additional slots, longitudinal recesses (formed along the entire length or a portion of the coupling feature), and other features. Some of such features can be used to reversibly mate the coupling feature with a tool actuation member (which is coupled to a tool driver's actuation member coupled to the coupling features), and to other elements of the surgical tool. Each coupling feature also has a coupling feature containment member disposed around the coupling feature.

Figure 9:
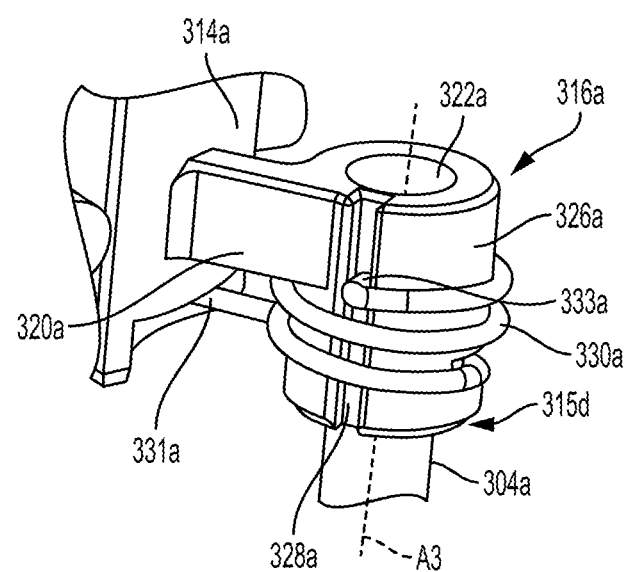
FIG. 9 is a perspective view of a coupling feature of the surgical tool, with the coupling feature being shown with a spring.

In the example illustrated, each of the coupling features 316a, 316b, 316c, 316d has a spring coupled therearound, such as, for example a spring 330a disposed around the coupling feature 316a as shown in FIG. 9. FIG. 11 illustrates an example of a spring 330 that can be disposed around any of the coupling features 316a, 316b, 316c, 316d. The spring 330, which can be a torsional spring, has a spring body 332 encompassing approximately two turns of the spring, a first, longer retention leg 331 and a second, shorter retention leg 333. In use, the first retention leg 331 is biased against the wall of an annular slot formed in the coupling feature having the spring 330' disposed therearound. For example, in FIG. 9 showing a spring 330a, disposed around the coupling feature 316a and configured in the same way as the spring 330 (FIG. 11), a first retention leg 331a of the spring 330a is biased against the annular slot 324a formed in the coupling feature 316a. FIG. 7 also illustrates that longer retention legs of the springs 330a, 330b, 330c disposed around the coupling features 316a, 316b, 316c are biased against the respective annular slots formed in the coupling features. The second retention leg 333, forming a substantially straight angle with the rest of the spring 330, is configured to be anchored in a longitudinal slot formed in the coupling feature. For example, FIG. 9 shows that a second retention leg 333a of the spring 330a is anchored in the longitudinal slot 328a of the coupling feature 316a. The engagement of the first retention leg 331a with the annular slot 324a and the engagement of the second retention leg 333a with the longitudinal slot 328a retains the spring 330a around the coupling feature 316a. The coupling features 316b, 316c, 316d have respective springs retained therearound in a similar manner.

Figure 8:
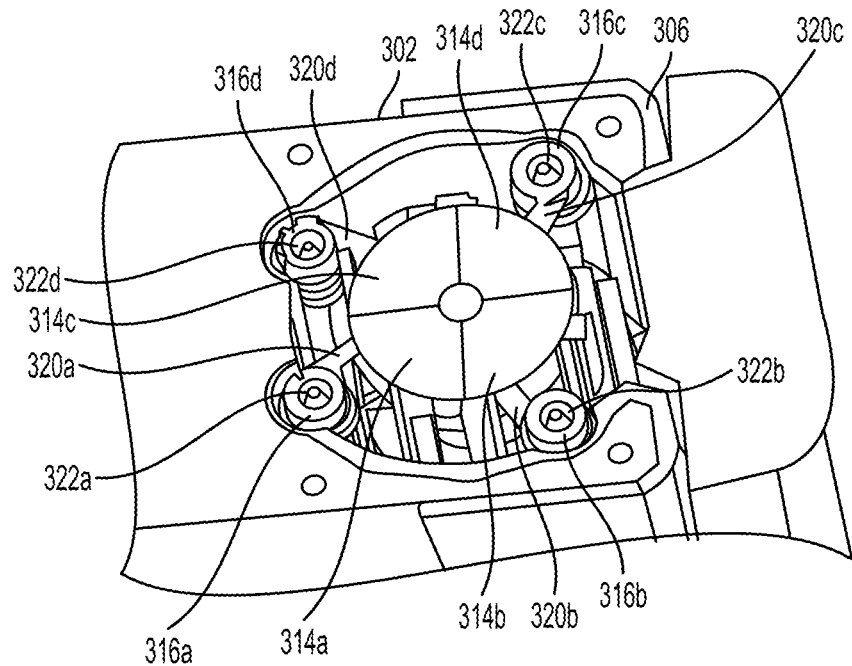
FIG. 8 is a partial view of surgical tool's coupling feature shown coupled with the tool driver's actuation members of FIG. 7.

As shown in FIGS. 5B, 7, and 8, each of the coupling features 316a, 316b, 316c, 316d of the surgical tool 300 is configured to reversibly engage with a proximal end of a corresponding actuation member from the plurality of actuation members 304a, 304b, 304c, 304d of the tool driver 302. The configuration of the reversible connection between the coupling features 316a, 316b, 316c, 316d and the actuation members 304a, 304b, 304c, 304d is such that it allows each of the actuation members to move both proximally ("pull" movement) and distally ("push" movement). This is achieved due to a reliable and straightforward way in which the actuation members are mated with the tool's coupling features. Also, the configuration of the described embodiments ensures an alignment between the actuation members and the tool's coupling features, which can be achieved in an intuitive way.

Once the actuation members are engaged with the tool's coupling features, the actuation members reversibly mate to the tool's actuation members such that the tool and the tool driver operably mate. The tool's actuation members can be, for example, ball screw actuators, though other configurations can be used additionally or alternatively. Thus, as the actuation members 304a, 304b, 304c, 304d are driven by one or more motors and are moved proximally and distally, the tool's actuation members coupled thereto translate these proximal and distal movements into proximal and distal movements of the tool's flexible members that are discussed above. In this way, movement of an end effector coupled to the tool's elongate shaft (e.g., the end effector 14 in FIG. 1) is effected and controlled.

In particular, all of the actuation members are configured to be simultaneously mated with the coupling features at a "neutral" position such that the actuation members are allowed to move independently from one another a certain distance proximally and distally. In this example, the distance is approximately 30 mm, though in other implementations the actuation members can be coupled to the tool so that they can move proximally and distally by other distances. Also, all of the actuation members can be simultaneously decoupled from the tool to thus allow separation of the surgical tool from the tool driver. The simultaneous decoupling is possible regardless of a particular position of each actuation member at that time.

The actuation members 304a, 304b, 304c, 304d of the tool driver 302 can have any of a variety of configurations. In addition, it should be appreciated that four actuation members 304a, 304b, 304c, 304d are shown by way of example only, as the tool driver 302 can have any other number of actuation members, e.g., less than four or greater than four.

As shown in FIG. 7, in the illustrated implementation, each actuation member is an elongate member extending proximally from the tool driver 302 towards the surgical tool 300. As shown in FIG. 13 illustrating an example of a proximal end 334 of an actuation member 304a (the actuation members 304b, 304c, 304d are configured similarly), the actuation member's proximal end 334 has a proximally-tapered tip 336 and a circumferential groove 338 spaced from a proximal-most tip 335 and disposed distally of the tapered tip 336 around the entire surface of the outer wall of the actuation member 304a.

With reference to FIG. 9, in use, when the actuation member 304a is inserted into an inner channel 322a of the coupling feature 316a through a distal end 315d of the coupling feature 316a, the actuation member's proximal end 334 (obscured in FIG. 9) engages the spring 330a. As discussed above, the spring 330a is biased against the wall of the coupling feature's annular slot 324a. When the inner channel 322a receives the actuation member 304a, the actuation member 304a is pushed against the spring 330a and thus causes the first retention leg 331a deflect outwardly until the actuation member's proximal end 334 clears the first retention leg 331a. Once cleared, the first retention leg 331a is able to snap back into its original position around the annular slot 324a of the coupling feature 316a. This occurs when the actuation member's circumferential groove 338 comes into alignment with the coupling feature's annular slot 324a and the first retention leg 331a is biased against the wall of the actuation member's circumferential groove 338 through the coupling feature's annular slot 324a. As mentioned above, the coupling feature has a coupling feature containment member (not shown) disposed around that coupling feature. The bias force of the spring 330a can be relatively small since, in the fully assembled configuration (not shown), the first retention leg 331a of the spring 330a is trapped between the actuation member's circumferential groove 338 and the coupling feature containment member.

Although the way in which one of the actuation members, the member 304a, is coupled with the coupling feature 316a is described above, it should be appreciated that the other three actuation members 304b, 304c, 304d are coupled with respective coupling features 316b, 316c, 316d in a similar manner. In this way, when the surgical tool 300 is brought into proximity of the tool driver 302, the actuation members 304a, 304b, 304c, 304d extending proximally from the tool driver 302 can simultaneously engage (e.g., snap into) the respective coupling features 316a, 316b, 316c, 316d. The proximal-most tips of the actuation members 304a, 304b, 304c, 304d disposed within the inner channels 322a, 322b, 322c, 322d of the coupling features 316a, 316b, 316c, 316d (FIG. 8) can then be engaged with the tool's actuation members (not shown) disposed within the tool's housing.

Figure 6:
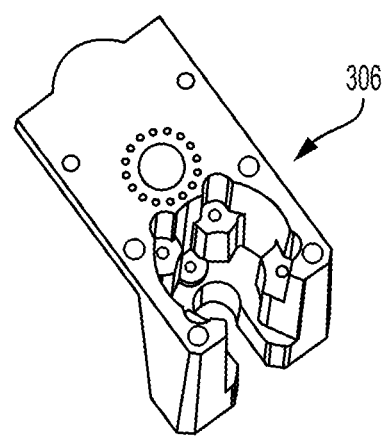
FIG. 6 is a perspective, partial view of the sterile barrier of FIG. 5A.

In the illustrated embodiments, as mentioned above, the tool 300 and the tool driver 302 are coupled through the sterile barrier 306 that is disposed therebetween, as shown in FIG. 5A. In the example illustrated, as shown in FIG. 6, the sterile barrier 306 is in the form of a substantially rigid container configured to receive a proximal portion of each of the actuation members. FIG. 8 shows that the sterile barrier is disposed within the tool driver 302 such that the surgical tool's mating interface 312 and the actuation members coupled to its coupling features are disposed within the sterile barrier 306. The actuation members disposed within the sterile barrier 306 can move therewithin proximally and distally, as discussed above.

Figure 14:
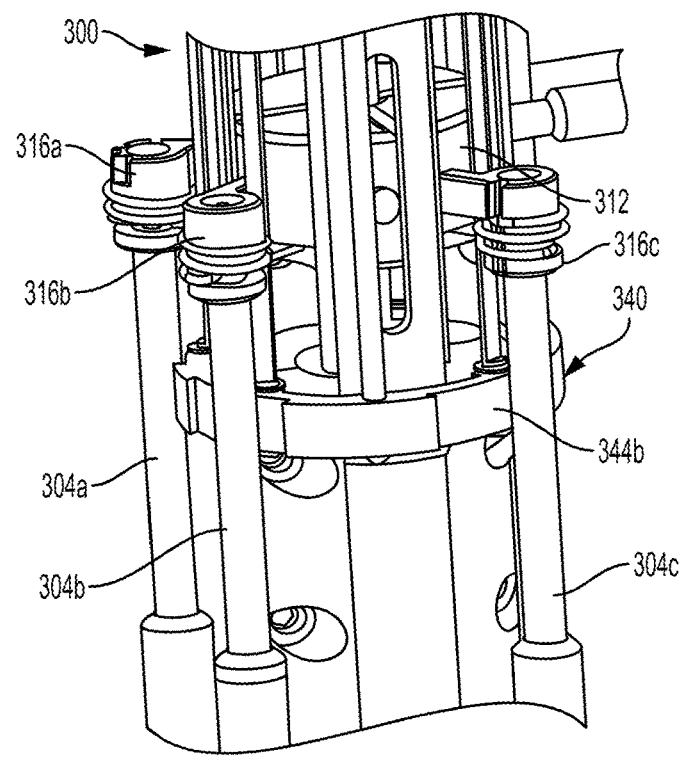
FIG. 14 is a perspective, partial view of the tool having a disengagement member, and of actuation members of the tool driver of FIG. 7.
Figure 15:
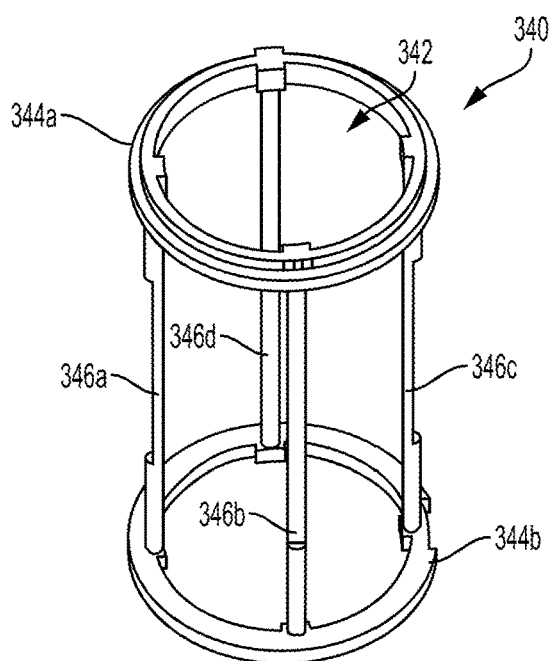
FIG. 15 is a perspective, partial view of the disengagement member of FIG. 14.

As also discussed above, the actuation members 304a, 304b, 304c, 304d of the tool driver 302 can be simultaneously coupled with the coupling features 316a, 316b, 316c, 316d of the surgical tool 300. Another advantage of the described techniques is that the actuation members 304a, 304b, 304c, 304d can also be simultaneously decoupled from the coupling features 316a, 316b, 316c, 316d of the surgical tool 300. In the described implementation, the robotic surgical tool 300 includes a component for the simultaneous decoupling of the actuation members 304a, 304b, 304c, 304d from the coupling features 316a, 316b, 316c, 316d. In particular, as shown in FIGS. 5B, 14, and 15, the tool 300 includes a movable disengagement member 340 configured to cause all of the plurality of actuation members to simultaneously disengage from the coupling features. In particular, the disengagement member 340 is configured to move the springs disposed around the coupling members that are used to retain the actuation members in engagement with the coupling members, as discussed in more detail below.

The disengagement member 340 can have various configurations. In this example, as shown in FIG. 15, the disengagement member 340, which can also be referred to as a "rotational cage," is in the form of a substantially open, generally cylindrical member having a passage 342 extending therethrough. The disengagement member 340 has first and second opposed ends 344a, 344b which are, in this example, substantially circular open members. The first and second opposed ends 344a, 344b are connected by a plurality of longitudinal struts 346a, 346b, 346c, 346d.

Figure 16B:
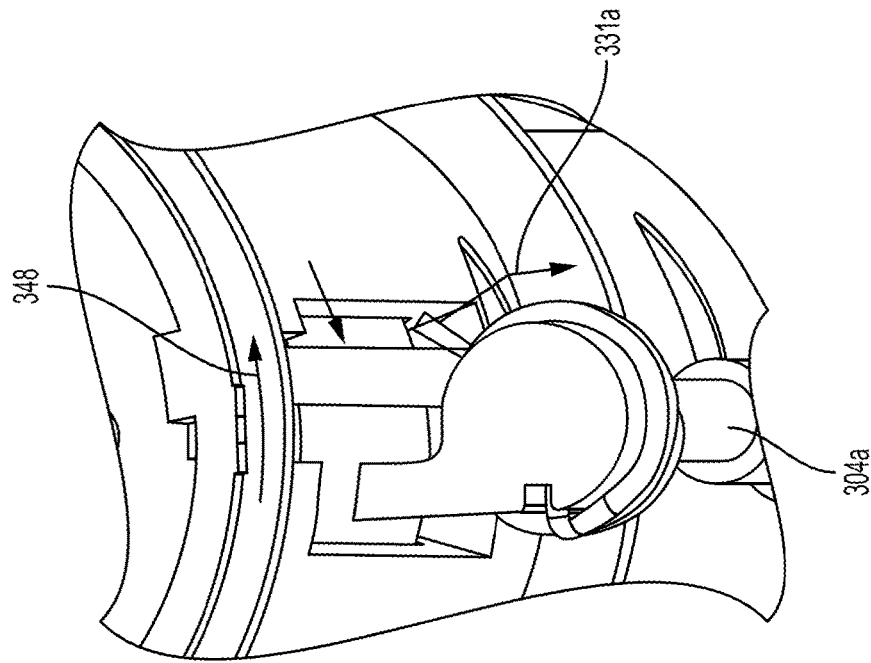
FIG. 16B is a perspective, partial view of the coupling feature of FIG. 16A, illustrating the spring of the coupling feature disengaged using the disengagement member of FIG. 15.
Figure 16A:
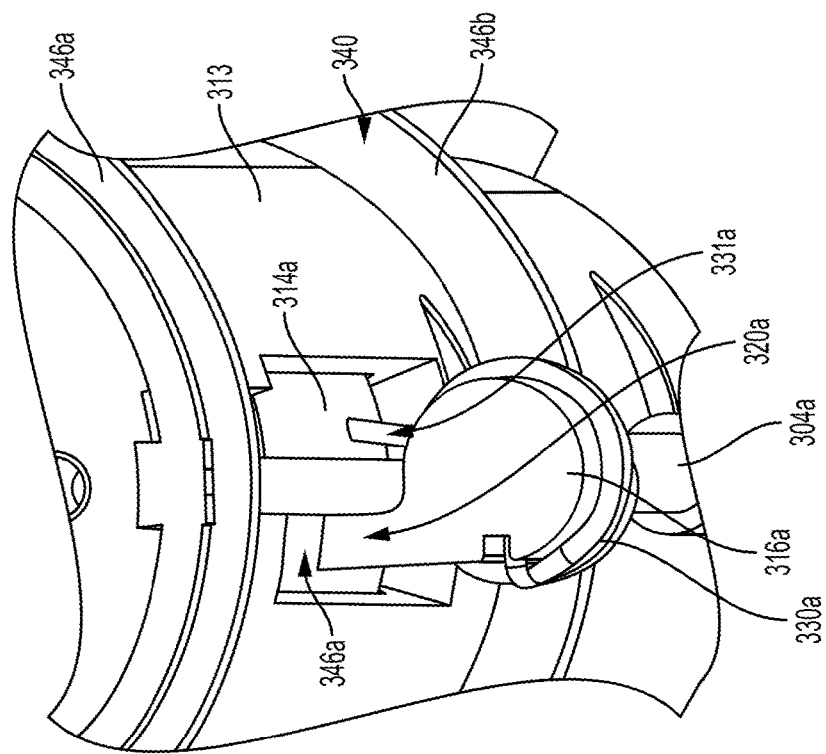
FIG. 16A is a perspective, partial view of a coupling feature of the tool FIG. 7, illustrating a spring of the coupling feature engaged with a corresponding actuation member of the tool driver of FIG. 7.

The disengagement member 340 is assembled around the tool body 313, as shown in FIGS. 5B and 14. Thus, before the decoupling step, the disengagement member 340 is disposed such that the longitudinal struts 346a, 346b, 346c, 346d are disposed between the coupling feature and the first retention leg of the spring disposed around that coupling feature, as shown in FIG. 14. In particular, as shown in more detail in FIG. 16A for the coupling feature 316a (shown without the disengagement member in FIG. 9), during operation of the tool 300 connected to a robotic surgical system via the tool driver 302, the longitudinal strut 346a of the disengagement member 340 is disposed between the outside wall of the tool body 313 and the coupling feature 316a. The coupling feature 316a is coupled to the movable portion 314a via the arm 320a. As also shown in FIG. 16A, the longitudinal strut 346a is nested between the coupling feature's arm 320a and the first retention leg 331a of the spring 330a. The other longitudinal struts 346b, 346c, 346d of the disengagement member 340 are similarly disposed around the tool body 313 in proximity to the coupling features 316b, 316c, 316d, respectively.

As shown in FIGS. 5B and 14, the elongate longitudinal struts 346a, 346b, 346c, 346d of the disengagement member 340 are disposed around the tool body 313 such that they do not interfere with linear movements of the actuation members engaged with the coupling features. Accordingly, the disengagement member 340 can be used to disengage the coupling feature's spring from engagement with the respective actuation member regardless of the position of the actuation member as it moves proximally or distally. Thus, in use, to simultaneously disengage the actuation members from the tool's coupling features, the disengagement member 340 is rotated via a suitable mechanism (e.g., a knob, handle, or any other actuator) in the direction shown by an arrow 348 in FIG. 16B and additionally in FIG. 12. With reference to FIG. 16B, the rotation of the disengagement member 340 causes the longitudinal strut 346a to contact the first retention leg 331a of the spring 330a and cause the leg 331a to move (or deflect) outwardly in the same direction.

In this way, with the spring 330a clears and releases or disengages the proximal end of the actuation member 304a.

Because of the configuration of the disengagement member 340, its rotation in the described manner causes all of the actuation members 304a, 304b, 304c, 304d of the tool driver 302 to be simultaneously decoupled from the coupling features 316a, 316b, 316c, 316d. The tool 300 can then be separated from the tool driver 302. Accordingly, the described techniques facilitate a low-force, intuitive simultaneous decoupling of the actuation members from the tool's coupling features, which can be advantageous during a surgical procedure when more than one surgical tool is to be loaded on the tool driver. This can also be advantageous if an event (e.g., a loss of power) occurs in the robotic surgical system which requires a simultaneous decoupling of the tool from the driver regardless of each actuation member's current position. Thus, even if an unexpected loss of power or other undesirable event occurs, the tool can be disconnected from the tool driver in an efficient and safe manner. Thus, the described implementations allow for a straightforward, low-force simultaneous coupling and decoupling of the actuation members with and from the tool's coupling features.

As mentioned above, the techniques described herein enable use of a surgical tool coupled to a tool driver of a robotic surgical system via a sterile barrier disposed between the tool and the tool driver. Thus, at least a portion of components of the tool driver, such as proximal portions of tool driver's actuation members, that are configured to couple with the tool are disposed within the sterile barrier. Because the actuation members can move proximally and distally independently from one another, the sterile barrier must allow for these movements while maintaining its structural integrity. Various components can be used to removably couple the tool with the tool driver through the sterile barrier in a way that allows for independent movements of the actuation members within the sterile barrier.

In some embodiments, a surgical tool can be coupled to a tool driver via sterile barrier couplers of a sterile barrier disposed between the tool and the tool driver. Each of the sterile barrier couplers can mate with the tool and the tool driver's actuation members. Also, in such embodiments, the sterile barrier couplers have bellows extending distally therefrom. The bellows are configured to stretch and contract with the linear movements of the actuation members of the tool driver. The sterile barrier couplers are configured to be simultaneously coupled to the actuation members to allow each actuation member to move proximally and distantly such that they can deliver both pull and push movements for tool's elements (e.g., the flexible members described above) that control operation of an end effector coupled to the tool. For example, in some implementations of the current subject matter, the actuation members can move proximally and distantly, independently from one another, a distance of about 30 mm. However, it should be appreciated that the actuation members can be configured to move a distance greater or less than 30 mm. The sterile barrier couplers are also configured to be simultaneously decoupled from the actuation members. In some embodiments described herein, a removable coupling system or member can be used to cause the sterile barrier couplers to be simultaneously coupled to or decoupled from the actuation members, as discussed below.

Figure 17:
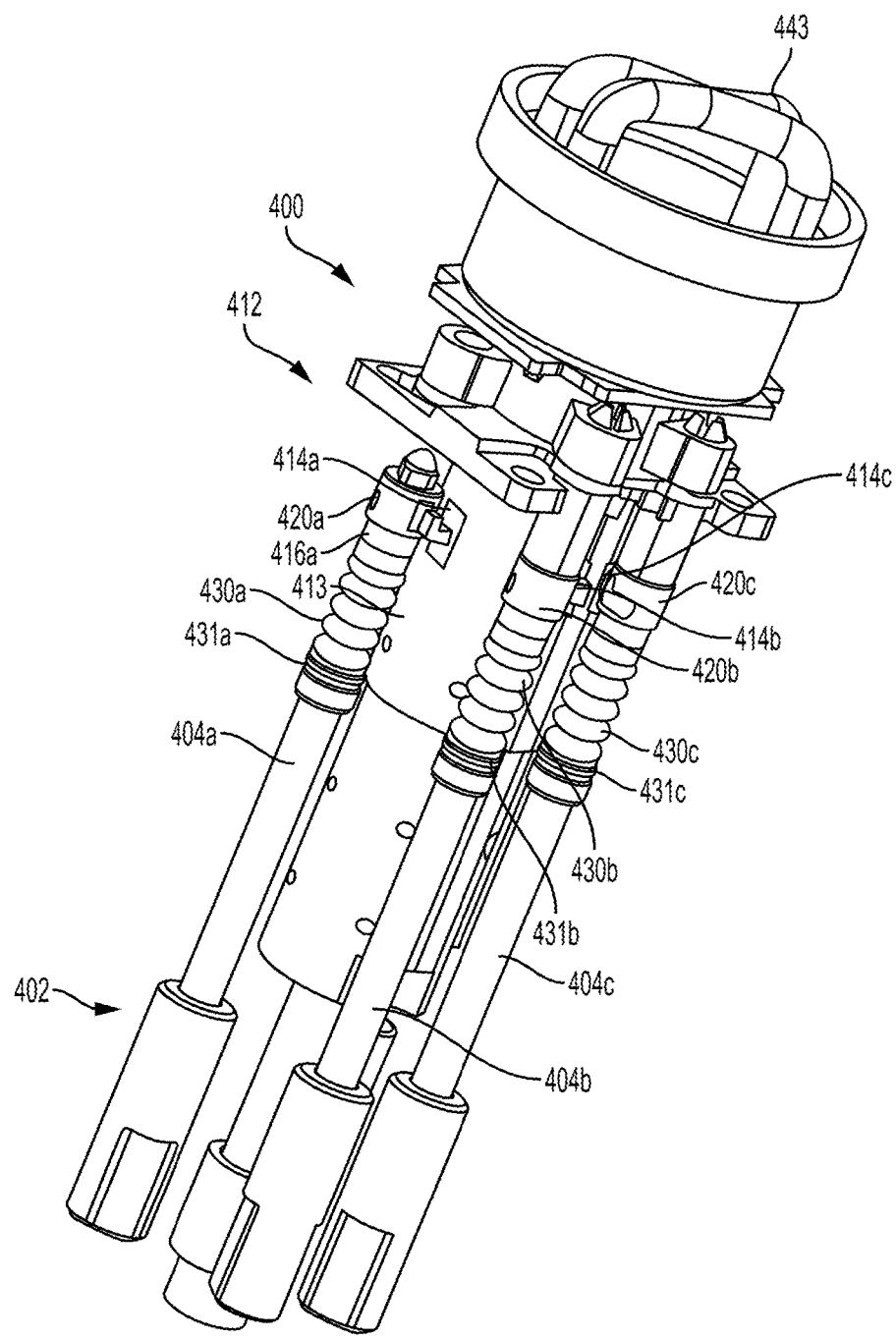
FIG. 17 is a perspective, partial view of another implementation of a proximal portion of a surgical tool, a tool driver, and a sterile barrier.
Figure 18:
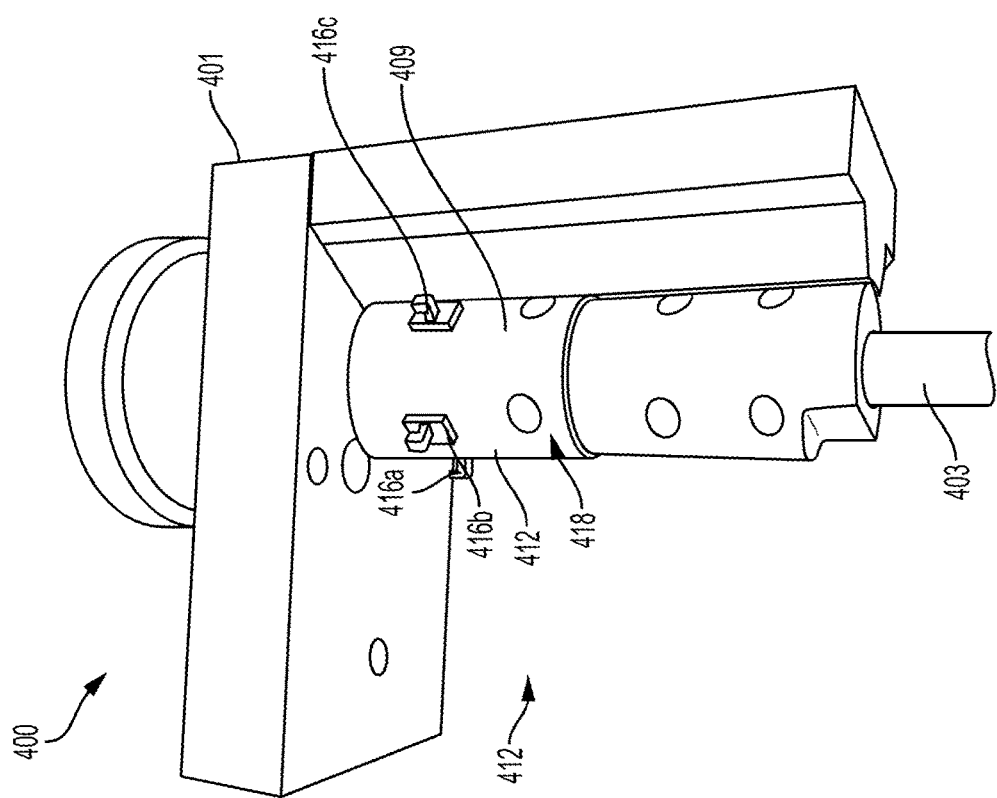
FIG. 18 is a perspective, partial view of the proximal portion of the surgical tool of FIG. 17.

FIGS. 17 and 18 illustrate another embodiment of a surgical tool 400 configured to reversibly mate with a tool driver 402 of a robotic surgical system. The surgical tool 400, a proximal portion of which is shown in FIGS. 17 and 18, has a housing 401 (shown in part in FIG. 18), an elongate shaft 403 extending distally from the housing 401, and an end effector (not shown) coupled to a distal end of the elongate shaft. The surgical tool 400 is configured to be removably mated with the tool driver 402 such that a sterile barrier is disposed between the tool 400 and the driver 402. Similar to the implementation described above, in this embodiment, four actuation members 404 of the tool driver 402 (of which three actuation members 404a, 404b, 404c are shown) are configured to be simultaneously coupled with the corresponding four coupling features 416 of the surgical tool 400, of which three coupling features 416a, 416b, 416c are shown in FIG. 18.

The sterile barrier 406 (shown in FIGS. 24C, 24D, 28A, 28B, 29A, and 29B) is configured to be disposed between the surgical tool 400 and the tool driver 402 so as to define a sterile side in which the surgical tool 400 is disposed and a non-sterile side in which a portion of the tool driver 402 is disposed. The sterile barrier 406, which can have a variety of configurations and which is at least partially disposed within the tool driver 402, encompasses the coupling features 416 engaged with proximal ends of the actuation members 404, as discussed in more detail below. Thus, components at the interface between the tool 400 and the tool driver 402 are disposed within the sterile barrier 406, which allows removing the tool 400 from the driver 402 and replacing it with another tool during a surgical procedure. The tool 400 can be a disposable tool or it can be a sterilizable tool that can be sterilized after each use and reused a certain number of times. The sterile barrier 406 is a disposable and replaceable element.

As shown in FIG. 18 illustrating the proximal portion of the surgical tool 400, the surgical tool 400 includes a mating interface 412 that has a plurality of tool plungers or movable portions 414 that are configured to move independently from one another. Three of the movable portions 414, movable portions 414a, 414b, and 414c, are shown in FIG. 17 where the fourth movable portion is obscured. In addition, FIG. 19 illustrates the movable portion 414a non-movably coupled with the coupling feature 416a. In the example illustrated, the movable portions 414 are in the form of elongate plungers disposed within a tool body 413 of the mating interface member 412. It should be appreciated that the mating interface member 412 can include other components that are not shown herein for clarity of description.

The coupling features 416 of the surgical tool 400 are disposed around a perimeter of an outer wall 418 of the mating interface member 412 such that each of the coupling features is attached to a corresponding one of the movable portions 414. In the illustrated implementation, the coupling features 416 are in the form of L-shaped members disposed around the outer wall 418 of the mating interface member 412, as shown in FIGS. 18 and 19. In some embodiments, the coupling features 416 can be formed integrally and/or monolithically formed with the movable portions 414.

Figure 19A:
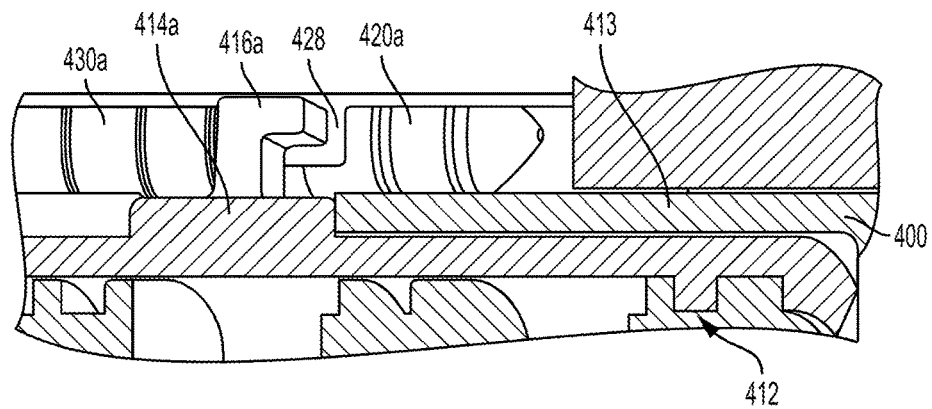
FIG. 19A is a perspective, partial view of the proximal portion of the surgical tool, tool driver, and sterile barrier of FIG. 17, illustrating a coupling feature of the tool disengaged from a sterile barrier coupler of the sterile barrier.
Figure 20:
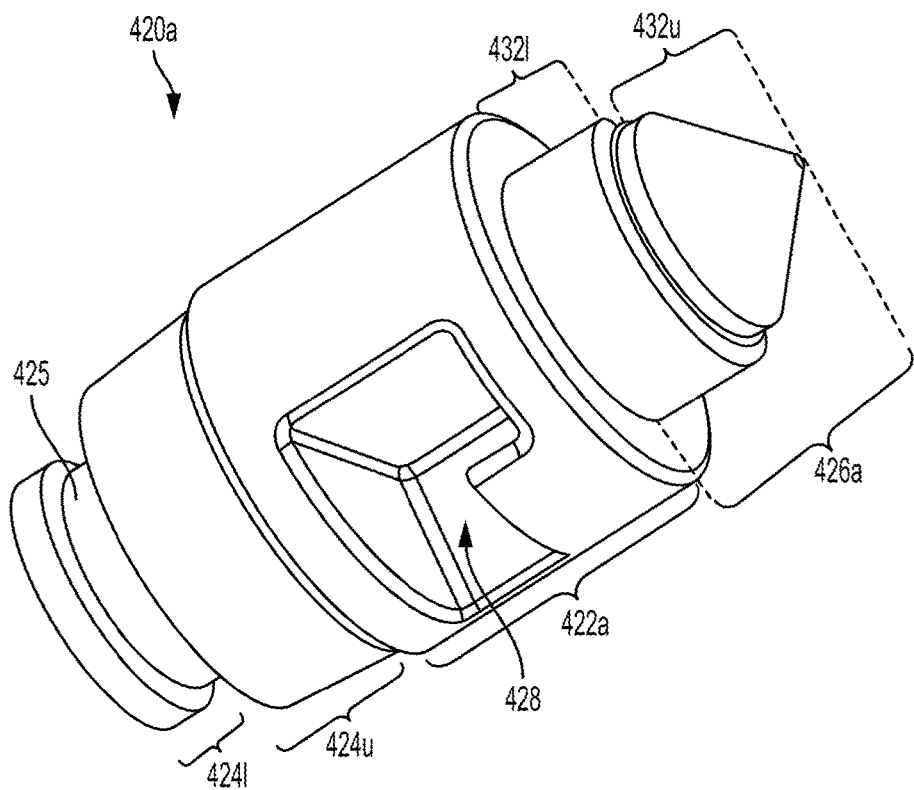
FIG. 20 is a perspective view of a sterile barrier coupler of the sterile barrier of FIG. 17.

In this implementation, each of the coupling features 416 is coupled to the proximal end of the actuation member of the actuation members 404 via a respective sterile barrier coupler 420. In the illustrated implementation, the tool 400 has a rotatable portion 409 configured to be rotated to cause the coupling features 416 to reversibly engage with the sterile barrier couplers 420, as discussed in more detail below. FIG. 18 illustrates three sterile barrier couplers 420a, 420b, 420c, with the fourth sterile barrier coupler being obscured. Also, the sterile barrier coupler 420a is shown in FIG. 19A and FIG. 20. The sterile barrier couplers 420 are configured to be simultaneously coupled with the actuation members 404 using a removable coupling member 440 which delivers the sterile barrier couplers. The removable coupling member 440, which is described in more detail below, is also used to simultaneously remove the sterile barrier couplers 420 from the actuation members 404.

Each of the sterile barrier couplers is part of the sterile barrier and has bellows extending distally therefrom that expand (e.g., stretch) and contract with the linear movement of the tool's drivers actuation members. Thus, as shown in FIG. 17, the sterile barrier couplers 420a, 420b, 420c have bellows 430a, 430b, 430c extending distally therefrom that encompass proximal portions of the actuation members 404a, 404b, 404c. As mentioned above, the fourth sterile barrier coupler 420d (shown in FIGS. 28A, 28B, 29A, and 29B) that also has respective bellows extending distally therefrom, as well as the coupling feature engaged therewith, are obscured in FIG. 17. Distal ends 431a, 431b, 431c of the bellows 430a, 430b, 430c (and of the bellows of the sterile barrier coupler 420d) define a distal end of the sterile barrier 406. Thus, the sterile barrier 406 is disposed at least partially within the tool driver 402 so as to encompass the bellows.

The sterile barrier coupler in accordance with the described techniques can have a variety of configurations. Also, each sterile barrier coupler 420 has a proximal portion configured to engage the coupling feature 416 and a distal portion configured to engage the proximal portion of the actuation member. In particular, as shown in FIG. 20 illustrating the sterile barrier coupler 420a as an example of the sterile barrier couplers 420, the sterile barrier coupler 420a is a generally cylindrical member having a proximal portion 422a, a distal portion 424a, and a proximal tip 426a extending proximally from the proximal portion 422a. The proximal portion 424a has an L-shaped pocket or recess 428 configured to engage the respective coupling feature 416a having the L-shape complementary to the shape of the L-shaped recess 428 (FIG. 17). It should be appreciated that the recess 428 can have other configurations, in which case the coupling feature to be engaged therewith will also have other configurations. While the process of engagement of the recess in the proximal portion of the sterile barrier coupler with the tool's coupling feature is described in more detail below, FIG. 19A shows the coupling feature 416a disengaged from the recess 428 and FIG. 19C illustrates the coupling feature 416a engaged with the recess 428.

The distal (or base) portion 424a of the sterile barrier coupler 420a configured to engage a proximal tip of the actuation member, in turn, includes lower and upper portions 4241, 424u as shown in FIG. 20. The upper portion 424u has a circumference that is approximately the same to that of the proximal portion 422a, whereas the lower portion 4241 has a smaller circumference than the upper portion 424u. Also, as shown in FIG. 20, the lower portion 4241 has an annular recess 425 configured to mate with a corresponding bellows.

Figure 21:
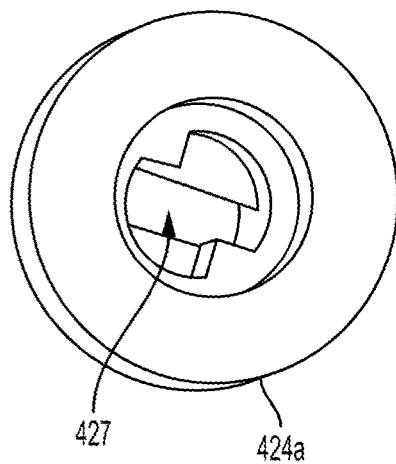
FIG. 21 is a perspective view of a distal portion of the sterile barrier coupler of FIG. 20.
Figure 22:
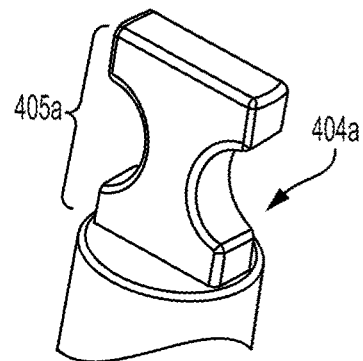
FIG. 22 is a perspective view of a proximal end of an actuation member of the tool driver of FIG. 17.

The distal portion 424a of the sterile barrier coupler 420a is configured to reversibly engage with the proximal tip of the actuation member, such as the actuation member 404a (FIG. 17), via a mating feature. In the illustrated embodiment, such mating feature is in the form of a quarter-turn T-shaped locking pocket or recess 427 extending through the distal portion 424a of the sterile barrier coupler 420a as shown in FIG. 21. The recess 427 is configured such that the proximal end of the actuation member 404a is received therein and it turned to be locked within the recess 427, thereby mating the actuation member with the sterile barrier coupler 420a. A proximal end 405a of the actuation member 404a is shown by way of example in FIG. 22. As shown, the proximal end 405a is generally T-shaped, with arcuate sides of the "T." It should be appreciated that the proximal ends of the other three actuation members 404b, 404c, 404d have the proximal tips configured in substantially the same manner.

In use, as discussed in more detail below, when the sterile barrier coupler 420a is loaded proximally onto the actuation member 404a, as discussed in more detail below, the "T" of the actuation member's proximal end 405a is received within the complementary, T-shaped locking recess 427. Upon turning the sterile barrier coupler 420a (in this example, a quarter-turn), the actuation member's proximal end 405a becomes lockingly engaged with the sterile barrier coupler 420a.

Figure 23:
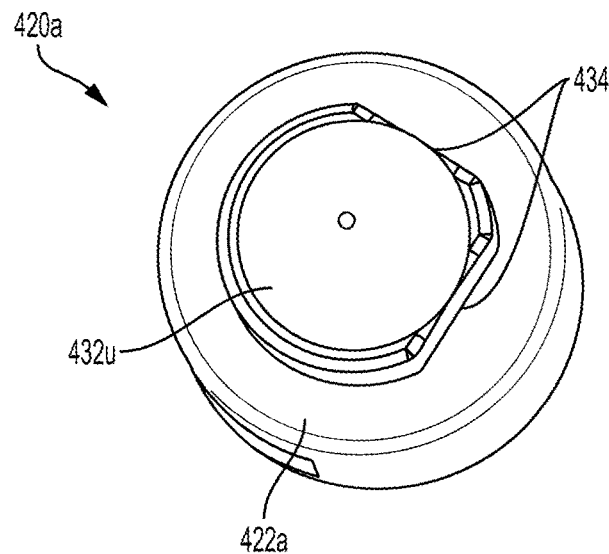
FIG. 23 is a perspective view of a proximal portion of the sterile barrier coupler of FIG. 20.

Referring back to FIG. 20, the proximal tip 426a of the sterile barrier coupler 420a includes a generally cylindrical lower portion 4321 and a proximally tapered, generally conical upper portion 432u. The upper portion 432u is generally conical. As shown in FIG. 23, the lower portion 4321 of the proximal tip 426a of the sterile barrier coupler 420a has flattened chord portions 434 configured to reversibly mate with a removable coupling member 440 for delivery of the sterile barrier coupler 420a to the actuation member 404a and removal of the sterile barrier coupler 420a from the actuation member 404a.

The removable coupling member 440, which is part of the sterile barrier 406 disposed in the assembled configuration between the surgical tool 400 and the tool driver 402, is shown in FIGS. 24A, 25A, 25B, 26A, and 26B. The removable coupling member 440 has a body 442, a rotatable actuator in the form of a handle 444 coupled on top of the body 442 and a generally circular gear 446 coupled to the bottom of the body 442 and configured to be rotated about a longitudinal axis B of the removable coupling member 440 upon rotation of the handle 442. The removable coupling member 440 also has coupling sleeves 448a, 448b, 448c, 448d extending from the bottom of the body 442 and configured to reversibly engage proximal tips of sterile barrier couplers. For example, the generally cylindrical coupling sleeves 448a, 448b, 448c, 448d can have a configuration complementary to the configuration of the proximal tips of the sterile barrier couplers 420 (such as, e.g., the proximal tip 426a of the sterile barrier coupler 420a). As also shown, the gear 446 has teeth 445 disposed around the outer wall thereof and engaged with the coupling sleeves 448a, 448b, 448c, 448d (e.g., via teeth or other features formed on outer walls of the coupling sleeves) to cause them to move upon rotation of the gear 446. Thus, in use, the rotatable handle 444 is configured to be rotated to move the gear 446, which, in turn, causes the coupling sleeves 448a, 448b, 448c, 448d to rotate. This causes the sterile barrier couplers 420 mated with the coupling sleeves to rotate as well so as to lock with the tool driver's actuation members, as described below.

In the illustrated implementation, the removable coupling member 440 is temporarily mated with the tool driver 402 as part of the sterile barrier 406. After the operation of delivering the sterile barrier couplers to the actuation members is completed, the removable coupling member 440 is removed from the sterile barrier 406. It should be appreciated that the removable coupling member 440 can have other components that are not described herein. Also, the removable coupling member 440 and one or more of its components can have various configurations that can be different from those illustrated herein. For example, the body 442 can have various other configurations. Similarly, the removable coupling member's actuator is shown in the form of the handle 444 by way of example only, as the actuator can have a variety of configurations. For example, FIG. 17 illustrates a handle 443 having a different configuration. The gear 446, as well as other components of the removable coupling member 440, can also have any suitable configurations that allow the removable coupling member 440 to be used to deliver the sterile barrier couplers to the tool driver and to lock the sterile barrier couplers onto the tool driver's actuation members.

Figure 24A:
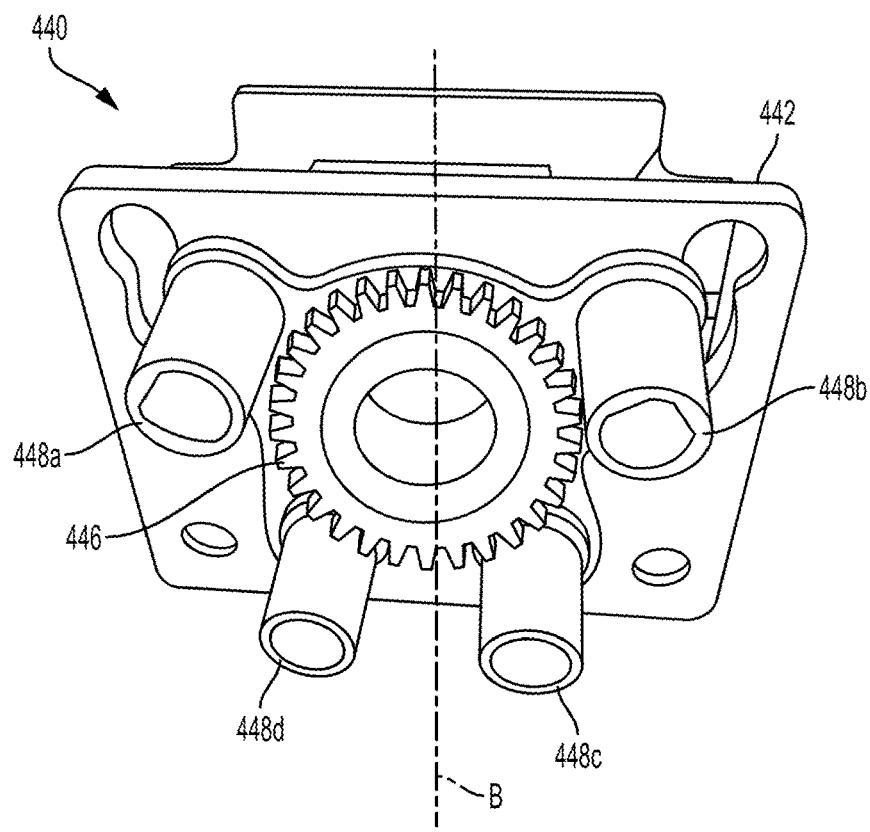
FIG. 24A is a perspective view of a removable coupling member.
Figure 24B:
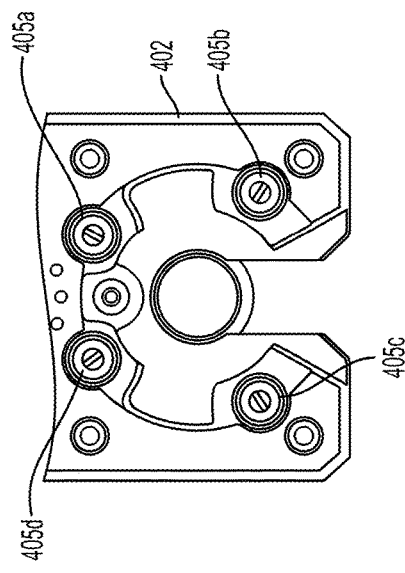
FIG. 24B is a cross-sectional, top view of the tool driver of FIG. 17, illustrating actuation members of the tool driver pre-positioned for engagement with sterile barrier couplers of the sterile barrier of FIG. 17.

In use, prior to loading the sterile barrier couplers 420a, 420b, 420c, 420d into the actuation members 404a, 404b, 404c, 404d, the coupling sleeves 448a, 448b, 448c, 448d of the removable coupling member 440 are engaged with the sterile barrier couplers 420a, 420b, 420c, 420d. FIG. 24B illustrates a cross-sectional top view of proximal ends 405a, 405b, 405c, 405d of the actuation members 404a, 404b, 404c, 404d before the sterile barrier couplers 420 are coupled thereto. In this figure, the actuation members 404a, 404b, 404c, 404d are in the "neutral" configuration in which the actuation members are pre-positioned for receiving the sterile barrier couplers.

The removable coupling member 440 with the sterile barrier couplers 420a, 420b, 420c, 420d loaded thereto is delivered to the tool driver's actuation members 404 pre-positioned as shown in FIG. 24B. The removable coupling member 440 is delivered to the tool driver's actuation members 404 as part of the sterile barrier 406 shown in FIG. 24C. The sterile barrier 406 can have any suitable configuration and, in this implementation, it can be a substantially rigid member encompassing the sterile barrier couplers and the bellows coupled thereto. Also, the sterile barrier 406 can have one or more portions made from a flexible fabric. For example, a draping feature of a suitable size and shape can be part of the sterile barrier 406.

Figure 24D:
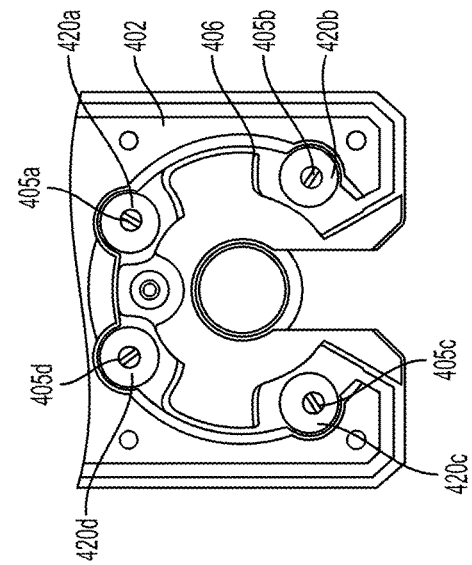
FIG. 24D is a cross-sectional, top view of the tool driver of FIG. 24c, illustrating the proximal ends of the actuation members locked within the recesses in the distal portions of the sterile barrier couplers.
Figure 24C:
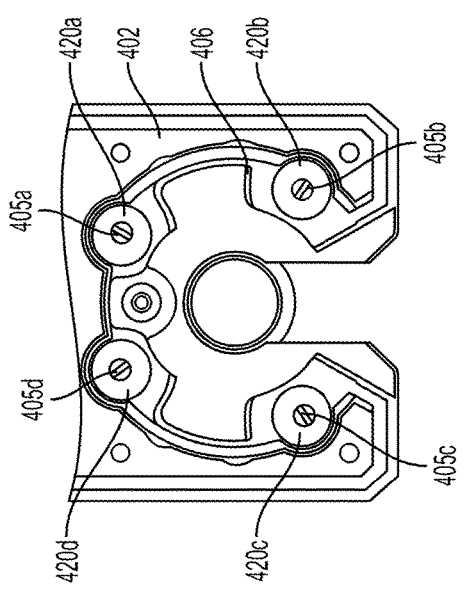
FIG. 24C is a cross-sectional, top view of the tool driver of FIG. 24B, illustrating proximal ends of the actuation members inserted into recesses in distal portions of the sterile barrier couplers.
Figure 25A:
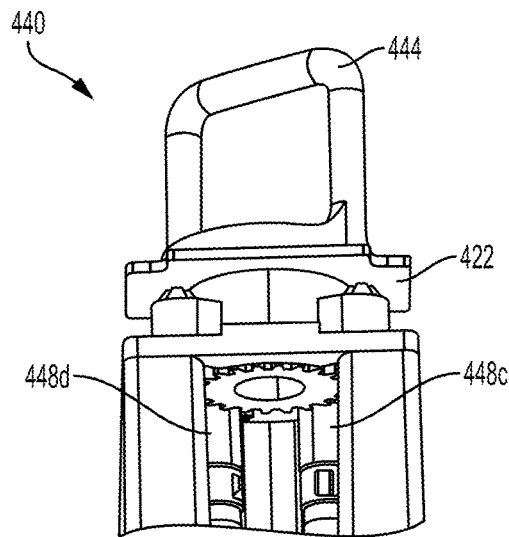
FIG. 25A is a perspective, partial view of a removable coupling member shown at a position in which the sterile barrier couplers held by the removable coupling member are disengaged from the actuation members of the tool driver.
Figure 25B:
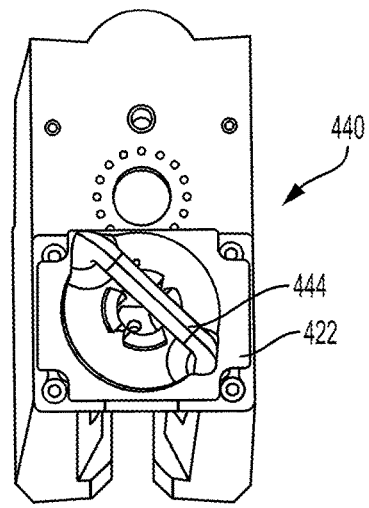
FIG. 25B is a top view of the removable coupling member of FIG. 25A.

FIG. 24C illustrates a cross-sectional top view the sterile barrier couplers 420a, 420b, 420c, 420d loaded onto the actuation members 404a, 404b, 404c, 404d, with the T-shaped recesses in the distal portions of the sterile barrier couplers (e.g., the recess 427 extending through the distal portion 424a of the sterile barrier coupler 420a, as shown in FIG. 21) shown aligned with the T-shaped proximal ends 405a, 405b, 405c, 405d of the actuation members 404. In this configuration, the removable coupling member 440 is in an un-coupled configuration as shown in FIGS. 25A and 25B.

Figure 26A:
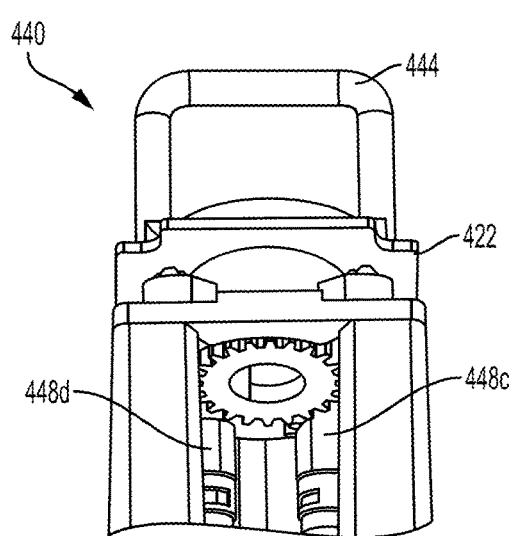
FIG. 26A is a perspective, partial view of the removable coupling member of FIGS. 25A and 25B shown at a position in which the sterile barrier couplers held by the removable coupling member are engaged from the actuation members of the tool driver upon actuation of the removable coupling member.
Figure 26B:
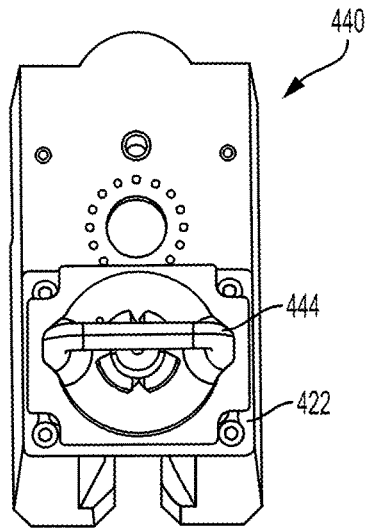
FIG. 26B is a top view of the removable coupling member of FIG. 26A.

After the sterile barrier couplers 420 are loaded onto the actuation members 404 such the sterile barrier couplers are seated over the proximal ends of the actuation members, the removable coupling member 440 is actuated (e.g., rotated) so as to change its configuration from un-coupled to a coupled configuration. To actuate the removable coupling member 440, its handle 444 is rotated so as to be positioned as shown in FIGS. 26A and 26B. The rotation of the handle 444 causes the gear 446 to rotate, thus rotating the coupling sleeves 448a, 448b, 448c, 448d (that are engaged with the sterile barrier couplers 420). As a result, the sterile barrier couplers 420 pre-loaded onto the actuation members are rotated and the T-shaped proximal ends 405a, 405b, 405c, 405d of the actuation members 404 become locked within the T-shaped recesses in the distal portions of the sterile barrier couplers 420, as shown in FIG. 24D. In this way, all of the sterile barrier couplers 420 of the sterile barrier 406 are simultaneously coupled with all of the tool driver's actuation members. Thus, the removable coupling member 440 allows coupling the sterile barrier 406 with the tool driver in a straightforward, error-prone, and efficient manner. After the removable coupling member 440 is used in this manner, it can removed from the tool driver 402, and the surgical tool 400 can be coupled with the tool driver 402 through the sterile barrier 406.

Referring back to FIG. 19A illustrating a portion of the tool 400 and the tool's coupling feature 416a, after sterile barrier 406 with the sterile barrier couplers 420 extending therethrough is coupled to the tool driver 402, the surgical tool 400 can be loaded onto the tool driver 402. The surgical tool 400 thus should be coupled to the tool driver 402 via the sterile barrier couplers 420. For this to occur, as discussed above, the sterile barrier couplers 420 must be engaged with the tool's coupling features. FIG. 19A illustrates the surgical tool 400 before the coupling feature 416a is mated with the recess 428 in the proximal portion 424a of the sterile barrier coupler 420a.

Figure 19B:
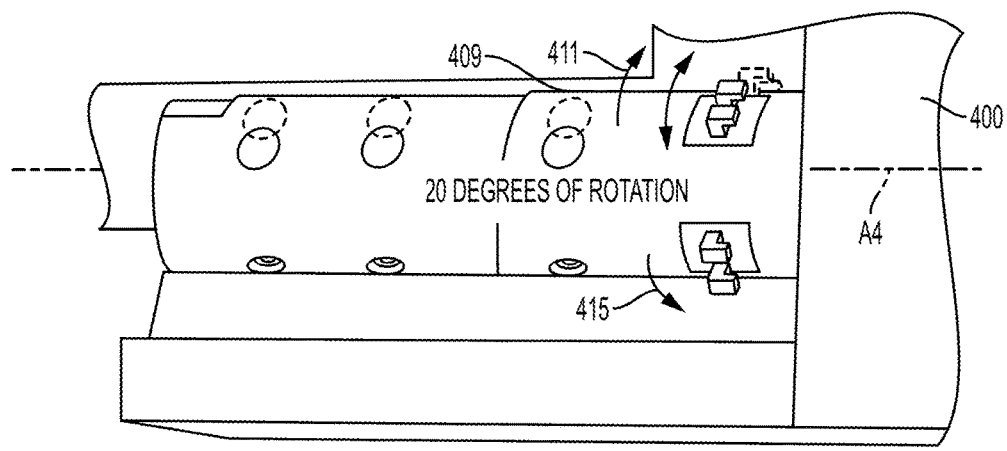
FIG. 19B is a perspective, partial view of the proximal portion of the surgical tool of FIG. 17, illustrating a rotatable portion of the tool.
Figure 19C:
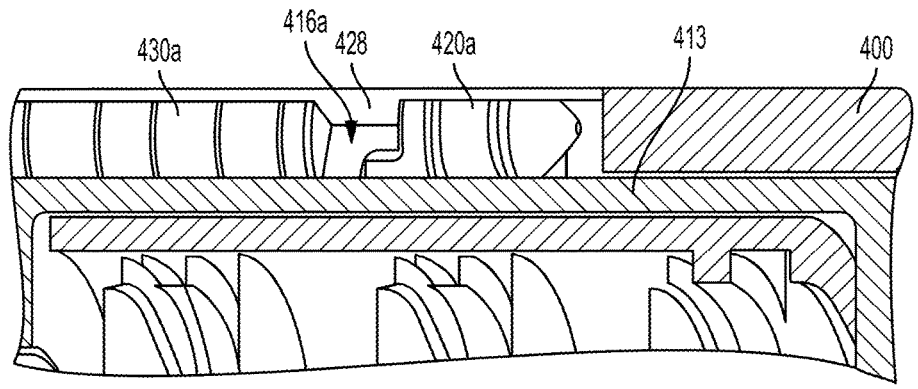
FIG. 19C is a perspective, partial view of the proximal portion of the surgical tool, tool driver, and sterile barrier of FIG. 19A, illustrating the coupling feature of the tool engaged with the sterile barrier coupler.
Figure 28A:
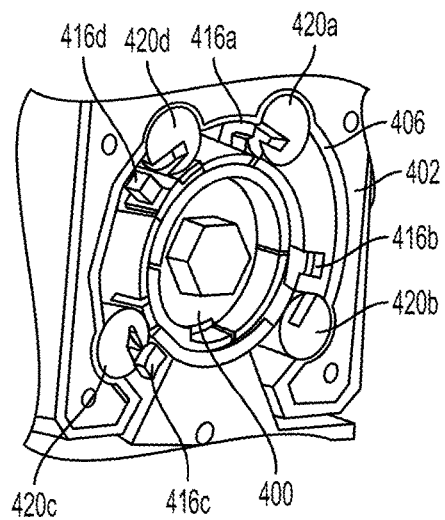
FIG. 28A is a partially cross-sectional view of the coupling features of the surgical tool and sterile barrier couplers of the sterile barrier of FIG. 17, illustrating the coupling features of the tool disengaged from the sterile barrier couplers.
Figure 28B:
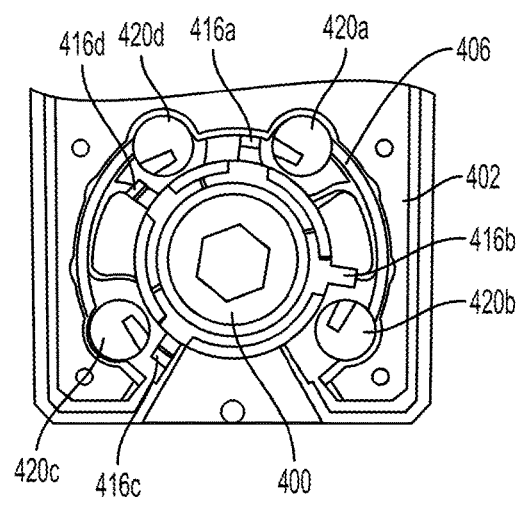
FIG. 28B is a top view of the coupling features and the sterile barrier couplers of FIG. 28A.
Figure 29A:
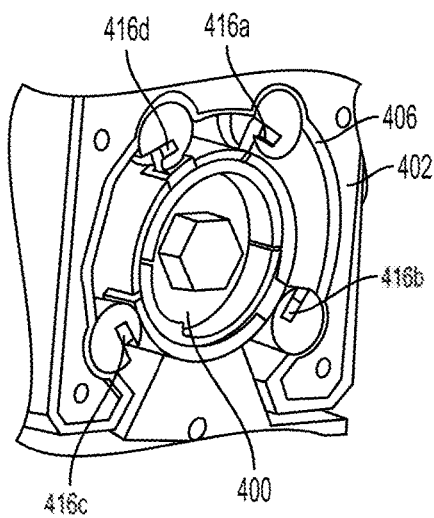
FIG. 29A is a partially cross-sectional view of the coupling features and the sterile barrier couplers of FIGS. 28A and 28B, illustrating the coupling features engaged with the sterile barrier couplers.
Figure 29B:
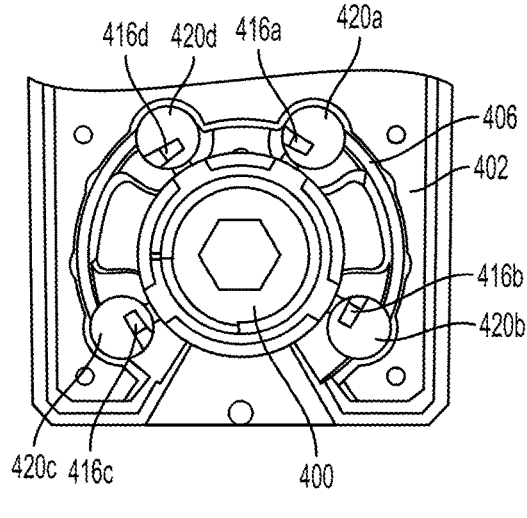
FIG. 29B is a top view of the coupling features and the sterile barrier couplers of FIG. 29A.

As shown in FIG. 19B, the surgical tool 400 can have a rotatable portion 409 disposed proximally of the elongate shaft 403 of the tool 400 and configured to be rotated about a longitudinal axis A4 of the tool 400 between a first position and a second position to thereby cause all of the coupling features to simultaneously engage with and simultaneously disengage from corresponding proximal portions of the sterile barrier couplers. The rotatable portion 409 is configured to be rotated to move between two pre-set configurations or positions—a non-coupled position in which the tool's coupling features are disengaged from the sterile barrier couplers and a coupled position in which the tool's coupling features are engaged with the sterile barrier couplers. The rotatable portion 409 can be configured to be rotated using a knob, a handle, or any other feature (not shown) configured to be operated by a user. When the surgical tool 400 is loaded onto the tool driver 402, the tool's coupling features and the movable portions are pre-positioned to a neutral/pre-load position in the un-coupled position of the tool 400. FIGS. 28A and 28B illustrate the tool's coupling features 416a, 416b, 416c, 416d disengaged from the sterile barrier couplers 420a, 420b, 420c, 420d.

Figure 27B:
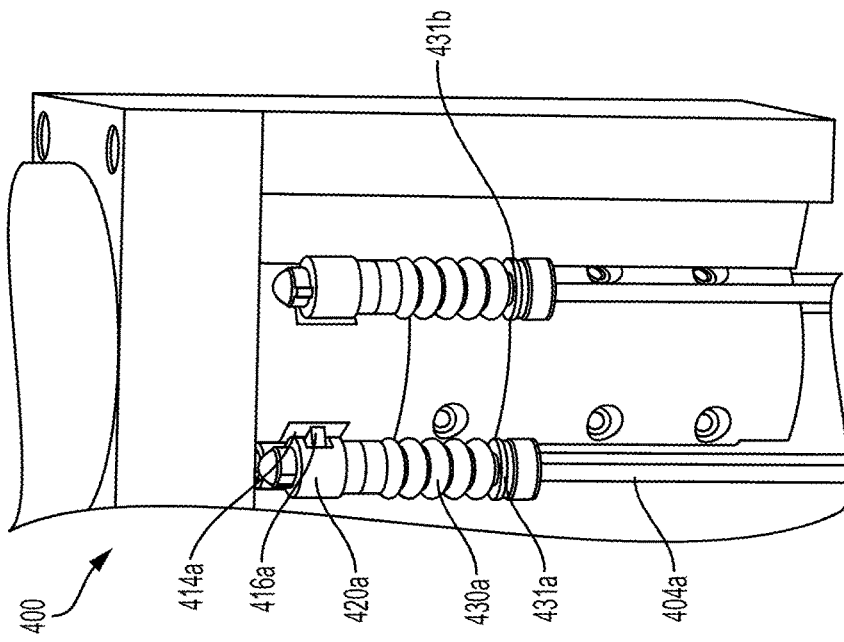
FIG. 27B is a perspective, partial view of the proximal portion of the surgical tool, tool driver, and sterile barrier of FIG. 27A, illustrating the coupling features of the tool engaged with the sterile barrier couplers of the sterile barrier.
Figure 27A:
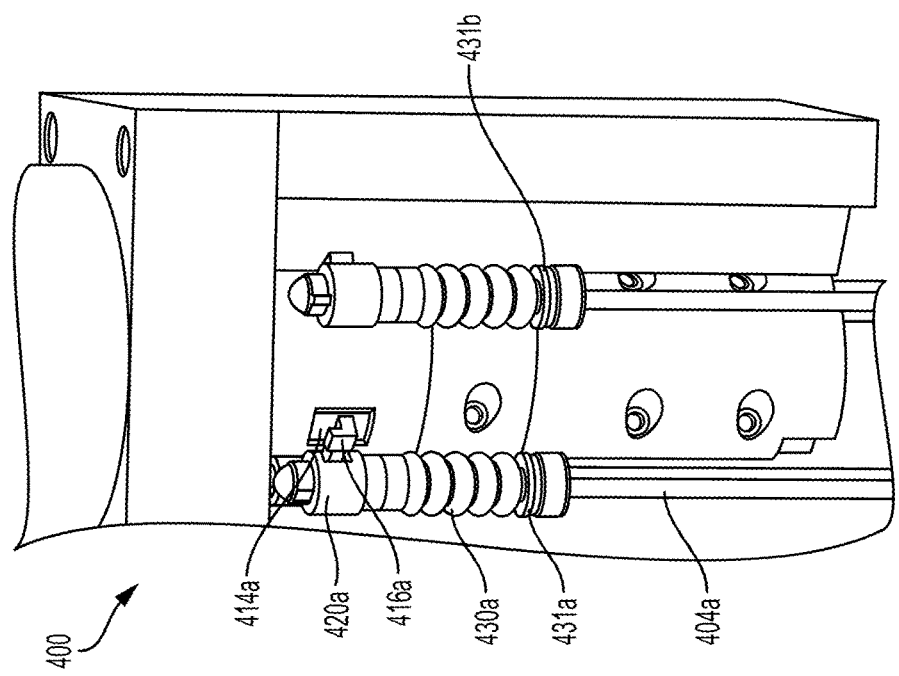
FIG. 27A is a perspective, partial view of the proximal portion of the surgical tool, tool driver, and sterile barrier of FIG. 17, illustrating the coupling features of the tool disengaged from the sterile barrier couplers of the sterile barrier.

After the tool 400 is rotated (in this example, about 20 degrees), the tool's coupling features become engaged with the sterile barrier couplers. In particular, as shown in FIG. 19C, upon rotation of the rotatable portion 409 of the tool 400 in a first direction (indicated by arrow 411 in FIG. 19B), the tool's coupling feature 416a becomes engaged with the recess 428 in the proximal portion 424a of the sterile barrier coupler 420a. At the same time, the other three coupling features 416b, 416c, 416d become engaged with the sterile barrier couplers 420. FIGS. 27A and 27B additionally illustrate the coupling feature 416a engaged with the sterile barrier coupler 420a (FIG. 27A) and the coupling feature 416a disengaged from the sterile barrier coupler 420a (FIG. 27B). FIGS. 28C and 28D illustrate the tool's coupling features 416a, 416b, 416c, 416d engaged with the sterile barrier couplers 420a, 420b, 420c, 420d.

In this way, all of the tool's coupling features 416 become simultaneously engaged with the sterile barrier couplers 420 having the bellows extending therefrom (e.g., the bellows 430a in FIG. 19A). The sterile barrier couplers 420 are engaged with the actuation members 404, as discussed above, and the bellows coupled to the sterile barrier couplers 420 encompass proximal portions of the actuation members. To engage the tool 400 with the tool driver 402 via the sterile barrier 406, the tool's actuation members (not shown) are engaged with the actuation members 404.

Once the tool 400 is coupled with the actuation members 404, the movable portions 414 allow the actuation members 404 to move proximally and distally independently from one another during normal operation of the tool 400 as part of the robotic surgical system. After the tool 400 is used as desired, it can be returned to its neutral position—i.e. a position in which the actuation members 404 are in their neutral position. The rotatable portion 409 of the tool 400 (FIG. 19B) can be rotated in a second direction indicated by an arrow 415 in FIG. 19B, where the second direction 415 is opposite to the first direction 411. This rotation causes the coupling members 416 of the tool 400 to disengage from the sterile barrier couplers 420, as shown in FIG. 19C. This can be done regardless of a specific position of each individual actuation member at a time when they are disconnected from the sterile barrier couplers 420. This can be particularly advantageous if an unexpected event, such as a loss of power, occurs, in which case the tool 400 can be safely removed from the tool driver 402.

The removable coupling member 440 can then be loaded onto the sterile barrier couplers 420, rotated to disengage the sterile barrier couplers 420 from the actuation members 404, and removed to separate the sterile barrier couplers 420 from the actuation members 404. In this way, all of the actuation members 404 are simultaneously decoupled from the sterile barrier couplers 420. The sterile barrier 406 can then be removed from the tool driver 402.

In the described implementations, techniques are provided for a method of operation of a surgical tool coupled with a tool driver of a robotic surgical system through a sterile barrier disposed therebetween. The sterile barrier is configured to prevent contamination of the robotic surgical system during a surgical procedure, and to limit the transfer of infectious agents from reusable components of the system to the patient. At the same time, robotic interfacing controls must operate the surgical tools through the sterile barrier. As discussed above, the tool can be reversibly mated with actuation members of the tool driver using the tool's coupling features or additionally using sterile barrier couplers. Components disposed at the interface between the tool and the tool driver operate within the sterile barrier. The sterile barrier can have various configurations and various types of components that allow independent translational movements of the tool driver's actuation members portions, of which are disposed within the sterile barrier.

In the described embodiments, as described in detail below, the sterile barrier can include a housing configured to accommodate proximal portions of a plurality of actuation members of a tool driver, and a plurality of substantially cylindrical, longitudinally expandable bellows disposed at least partially within the housing and each configured to encompass and mate with a proximal portion of a corresponding one of the plurality of actuation members.

Figure 30:
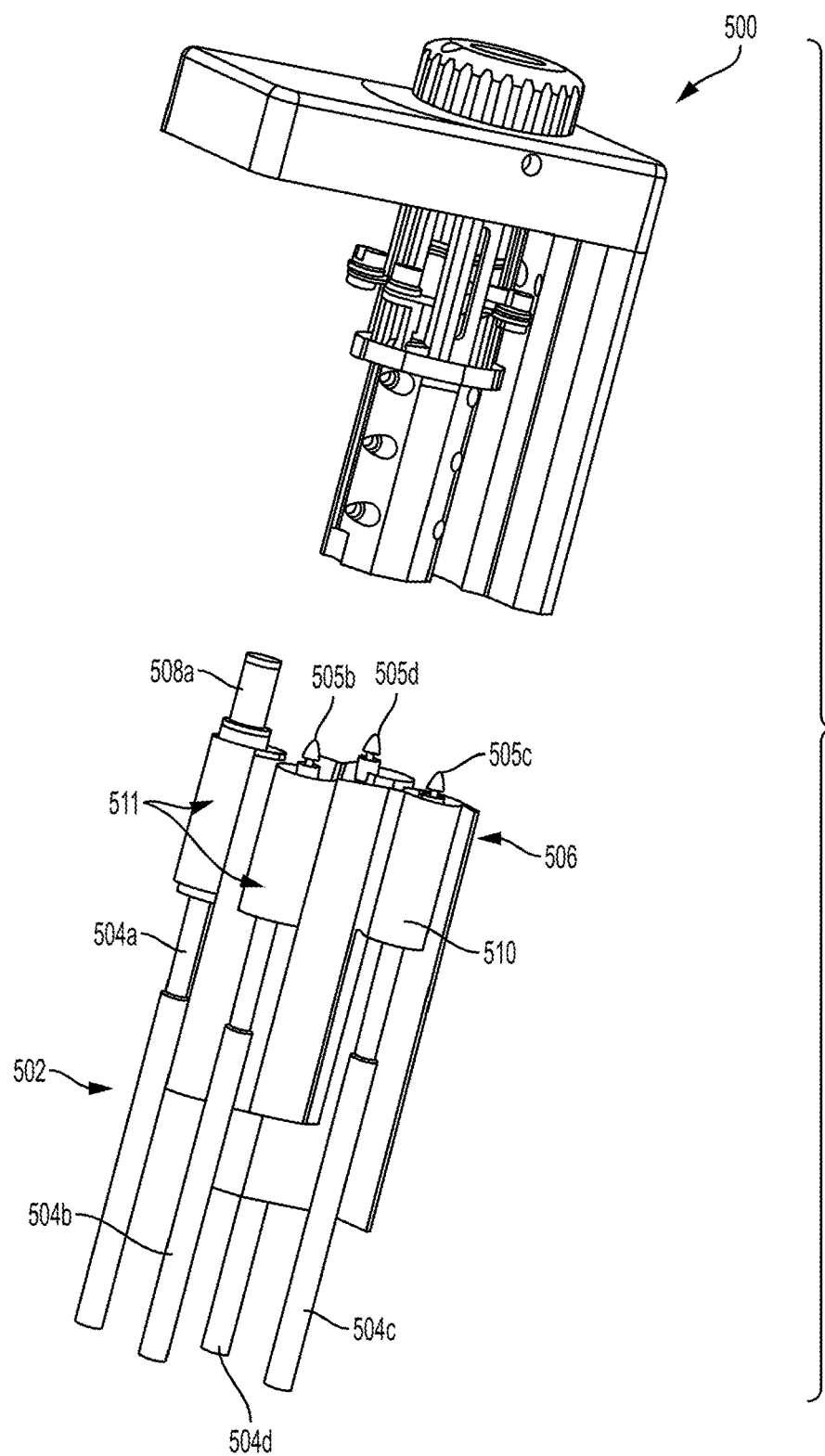
FIG. 30 is a perspective, partial view of another implementation of a proximal portion of a surgical tool, tool driver, and sterile barrier.

In some implementations, the actuation members and the tool's coupling features can mate within bellows elements disposed over proximal portions of the actuation members. FIG. 30 illustrates a proximal portion of a surgical tool 500 which can be similar to the surgical tool 300 (FIG. 5B). The surgical tool 500 is configured to removably mate with a tool driver 502, a proximal portion of which is shown as actuation members 504a, 504b, 504c, 504d, via a sterile barrier 506. Proximal ends 504b, 504c, 504d of the actuation members 504b, 504c, 504d are protruding from a housing 510 of the sterile barrier 506 in FIG. 30, whereas the proximal end of the actuation member 504a is encompassed by (and mated with) a bellows 508a discussed below. The housing 510 of the sterile barrier 506 can be a substantially rigid (e.g., plastic) component, and, in some embodiments, it can have a flexible fabric component (e.g., a draping feature) of a desirable and/or deformable shape coupled thereto in a suitable way, such as using an adhesive material.

As shown in FIG. 30, the housing 510 has a plurality of longitudinal, generally cylindrical enclosure portions 511 each configured to receive therethrough the proximal portion of the corresponding actuation member. It should be appreciated that in the assembled configuration as used during a surgical procedure, the proximal ends of all of the actuation members 504a, 504b, 504c, 504d are disposed within corresponding bellows-type elements.

Figure 31:
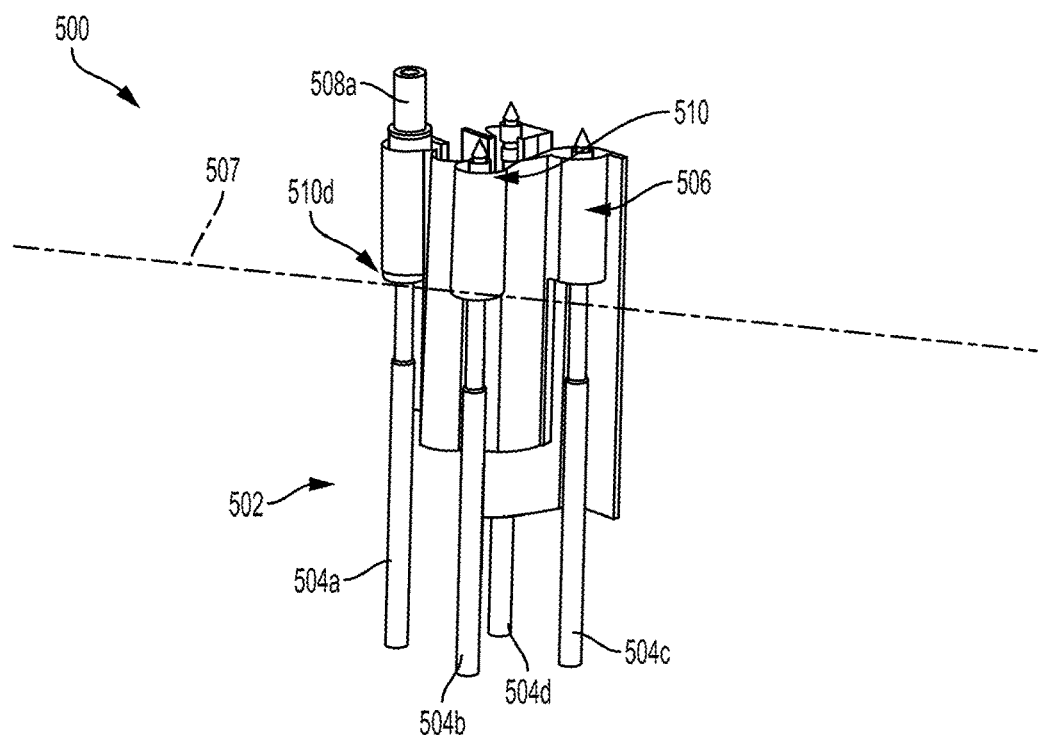
FIG. 31 is a schematic diagram illustrating relative positions of the surgical tool, tool driver, and sterile barrier of FIG. 30.

FIG. 31 illustrates the sterile barrier 506 with the actuation members 504a, 504b, 504c, 504d extending partially therethrough. A line 507 in FIG. 31 schematically illustrates a location of the tool 500 relative to the tool driver 502. In particular, the tool (not shown in FIG. 31) is loaded in the area above the line 507, and the tool driver 502 (of which only the actuation members are shown in FIG. 31) is located in the area below the line 507. As shown, the sterile barrier 506 is disposed between the tool 500 and the tool driver 502 such that the bellows encompassing proximal portions of the tool driver's actuation members are disposed entirely within the sterile barrier 506. Distal ends of the bellows are coupled to the sterile barrier 506, as discussed in more detail below.

Figure 32:
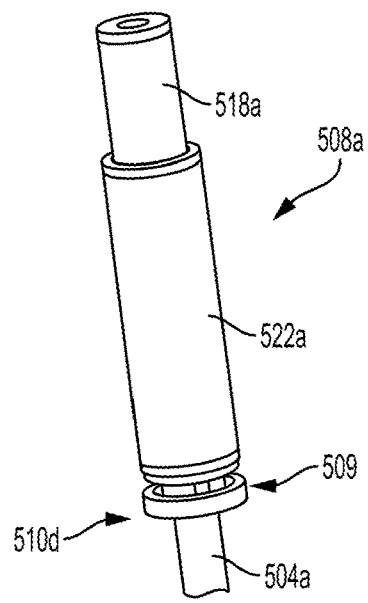
FIG. 32 is a perspective view of an actuation member of the tool driver of FIG. 30, showing the actuation member being coupled to a bellows of the sterile barrier of FIG. 30.

FIG. 32 illustrates, as an example, the bellows 508a having the proximal portion of the actuation member 504a extending therethrough. The bellows 508a, which illustrates just one example of the plurality of the bellows of the sterile barrier 506, can be in the form of substantially cylindrical, longitudinally expandable elements disposed at least partially within the housing 510 (FIGS. 30 and 31) and configured to encompass and mate with a proximal portion of a corresponding actuation member 504a. The bellows 508a can be formed from an elastomeric material.

The bellows 508a can allow the proximal portion of the actuation member 504a extending therethrough to move therewithin in proximal and distal directions such that the actuation member 504a moves independently from other actuation members of the tool driver. As shown, the bellows 508a has inner and outer portions 518a, 522a, the inner portion 518a being disposed at least partially within the outer portion 522a and being configured to move longitudinally within the outer portion 522a to adjust the length of the bellows 508a. FIG. 32 shows the inner portion 518a extending proximally from the outer portion 522a. The inner portion 518a can be coupled to the outer portion 522a in any suitable way. For example, the bellows can be molded as one piece and rolled or telescoped inside itself. A distal end 509 of the bellows 508a, in particular, a distal end 523 of the outer portion 522a, is coupled to a distal end 510d of the housing 510 of the sterile barrier 506. This can be done in any of various ways. In the illustrated embodiments, for example, the outer portion 522a is coupled to the distal end 510d via an insert feature 524 and via a snap ring 540, as discussed below.

Figure 33A:
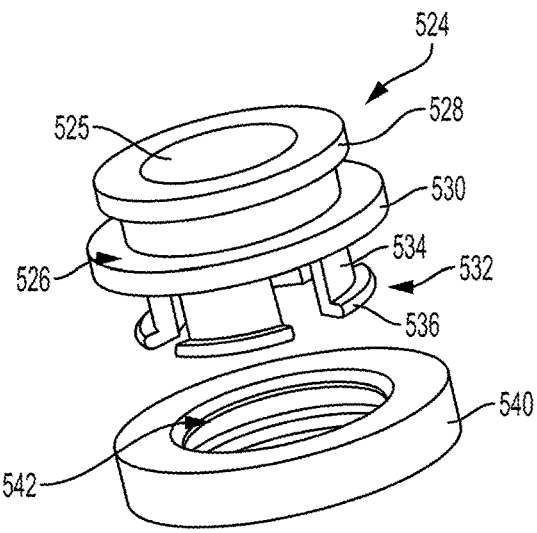
FIG. 33A is a perspective view of a coupling feature and ring configured to couple a distal end of a bellows to a distal end of the sterile barrier of FIG. 30.
Figure 33B:
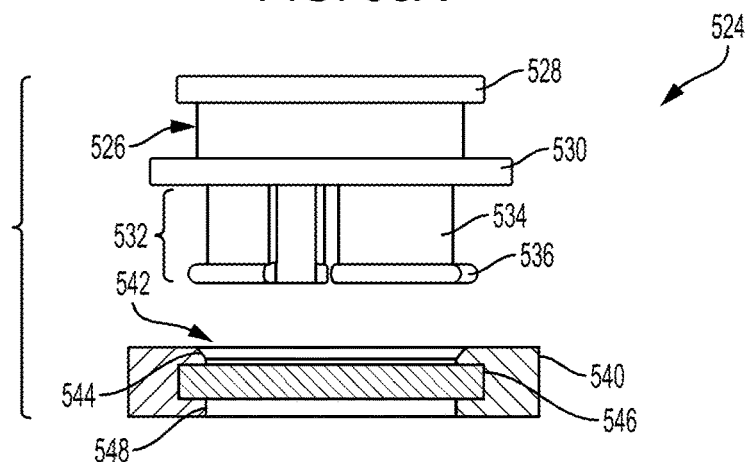
FIG. 33B is a side, cross-sectional view of the coupling feature and ring of FIG. 33A.

As shown in FIGS. 33A and 33B, the insert feature 524 having a channel 525 includes an annular groove 526 disposed between a first (top) annular ring 528 and a second (bottom) annular ring 530 that has a diameter greater than that of the first annular ring 528. The insert feature 524 also includes arm features 532 extending distally from the second annular ring 530 and each having a body 534 and a ridge 536 extending outwardly from a distal end of the body. In this example, the insert feature 524 has four arm features 532, though it should be appreciated that the insert feature 524 can have another suitable number (e.g., less than four or greater than four) of arm features or other features. As shown in FIG. 33B, an outer diameter of the arm features 532, measured as an outer diameter of the ridges 536 is approximately the same as the outer diameter of the first annular ring 528 and is less than the outer diameter of the second annular ring 530. As shown in FIG. 33B, the ring 540 has an opening 542 that has inner walls shaped such that the opening includes a slanted proximal portion 544, a straight-wall mid-portion 546, and a straight-wall distal portion 548. As shown, the mid-portion 546 has a greater diameter than each of the slanted proximal portion 544 and the distal portion 548, and the distal end of the proximal portion 544 has the same diameter as the distal portion 548. It should be appreciated that the ring 540 and its opening 542 can additionally or alternatively have a variety of other configurations and feature(s).

Figure 34:
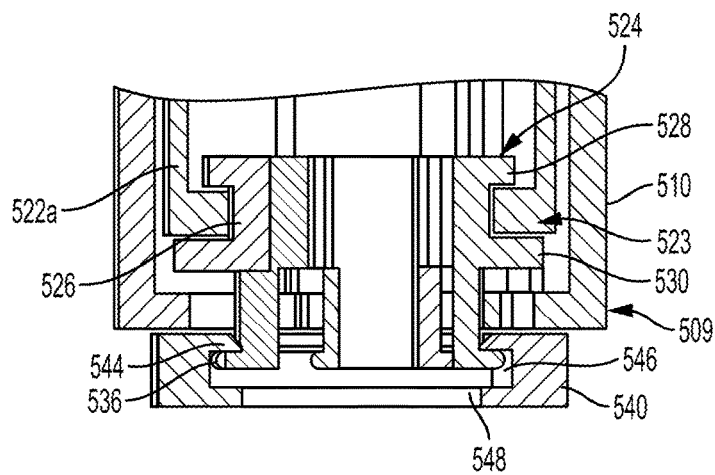
FIG. 34 is a side, cross-sectional view illustrating the coupling feature and ring of FIG. 33A applied to couple the distal end of the bellows to the distal end of the sterile barrier of FIG. 30.

In use, the insert feature 524 is coupled to the bellows 508a, and the bellows 508 with the insert feature 524 coupled thereto is inserted into the sterile barrier housing 510. The snap ring 540 is then engaged with a distal portion of the insert feature 524 that protrudes distally from the distal end of the sterile barrier housing 510. In particular, in order to attach the outer portion 522a of the bellows 508a to the distal end 510d of the sterile barrier's housing 510, the insert feature 524 is disposed such that it extends through the distal end 509 of the bellows 508a and through the distal end 510a of the sterile barrier's housing 510, as shown in FIG. 34. In particular, as also shown in FIG. 34, the distal end 523 of the outer portion 522a (having an inwardly extending inner rim) sits in the annular groove 526 between the first and second annular rings 528, 530 of the insert feature 524. The arm features 532 extend through the distal end 509 of the sterile barrier's housing 510. The snap ring 540 is disposed over a distal portion of the insert feature 524 extending from the distal end 509 of the housing 510. Thus, as shown in FIG. 34, the ridges 536 of the arm features 532 sit in the mid-portion 546 of the opening 542 of the snap ring 540 to thereby retain the bellows 508 in engagement with the sterile barrier 506.

After the bellows is engaged with the sterile barrier as discussed above, the sterile barrier 506 can be coupled to the tool driver 502. The actuation members of the tool driver 502 are inserted distally into the bellows, as shown in FIGS. 35A-35C. For example, with reference to FIG. 34, the actuation member 504a can be inserted into (e.g., pushed through) the bellows 508a through an opening extending into the distal portion 548. To later remove the actuation member 504a from the bellows 508a after use, sufficient force can be applied to pull the actuation member 504a off the bellows 508a, which actions allows wiping off the actuation member 504a as it slides off from the bellows 508a.

Each of the actuation members of the tool driver 502 engages with the inner portion of the bellows coupled to the distal end of the sterile barrier 506. In the illustrated implementation, the inner portion of the bellows rolls in and out within the bellows' outer portion that, in turn, does not move proximally and distally but can be rotated.

The actuation members can be coupled to the inner portion of the bellows in a number of different ways. Each actuation member can have any suitable mating feature(s) configured to reversibly mate with the inner portion of the bellows. For example, as shown in FIGS. 35A-35C, a proximal portion of the actuation member 504a of the tool driver 502 has an annular groove 550 formed in the outer wall thereof. The annular groove 550 is configured to mate with an engagement feature 519 in the form of an inwardly extending shoulder at a proximal end 521 of the inner portion 518a of the bellows 508a that is configured to fit within the annular groove 550. Thus, as the actuation member 504a is being inserted distally through the bellows 508, the annular groove 550 of the actuation member 504a becomes engaged with the engagement feature 519 of the inner portion 518a of the bellows 508a. In this way, when the actuation member 504a moves proximally and distally (up and down), the inner portion 518a of the bellows 508a coupled thereto follows movement of the actuation by extending and compressing accordingly. Other actuation members of the tool driver 502 are coupled to a respective bellows in a similar manner. It should be appreciated that the engagement interface between the actuation member 550 and bellows 519 can include other components that are not shown herein for clarity of description.

FIGS. 35A-35C illustrate by way of example different positions of the actuation member 504a coupled to and extending through the bellows 508a. Thus, FIG. 35A shows the most proximal position of the actuation member 504a, FIG. 35B shows normal, "home" position of the actuation member 504a, and FIG. 35C illustrates the most distal position of the actuation member 504a. It should be appreciated that the "proximal" and "distal" positions are referred to in this way for description purposes only, consistent with the proximal end of the actuation member being closer to the surgical tool (proximal position) or being farther away from surgical tool (distal position). At the same time, during the use of the surgical tool in the robotic surgical system, the actuation members can be oriented differently, such that the proximal and distal positions can be referred to as distal and proximal, respectively. Additionally, the actuation member 504a extending through the bellows 508a can be rotated since it is disposed within the bellows 508a with a clearance fit, as shown in FIGS. 35A-35C.

Figure 36:
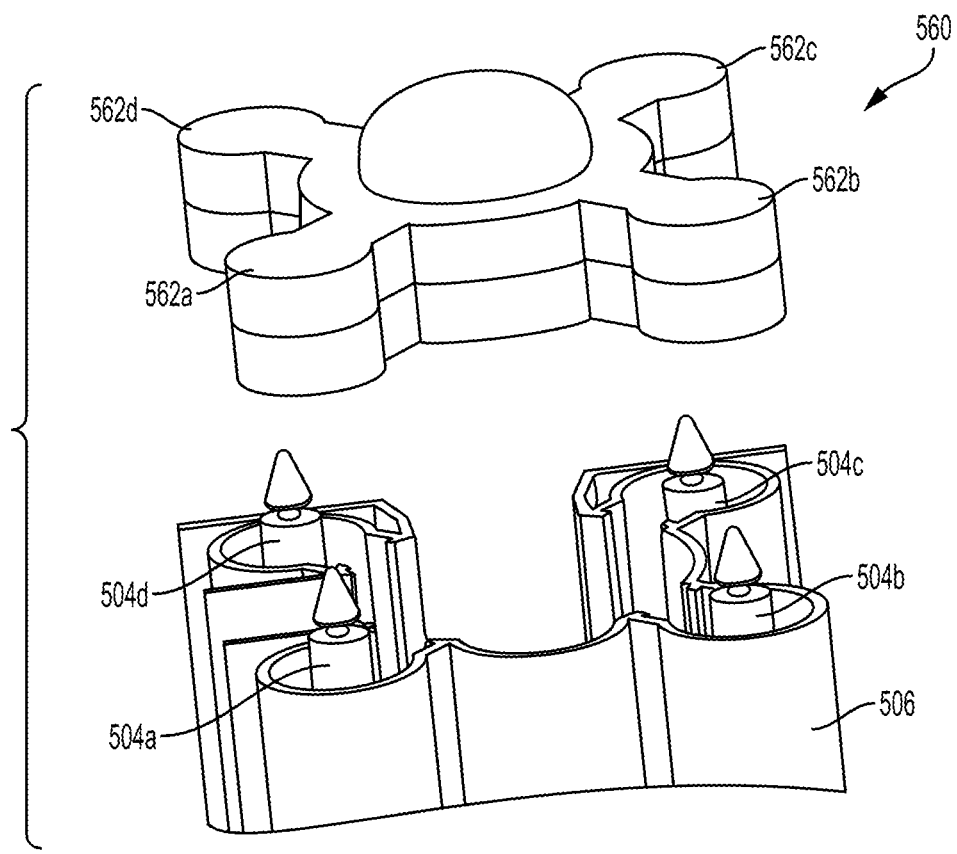
FIG. 36 is a perspective view of a cleaning device configured to clean proximal tips of the actuation members of FIG. 30.

In the illustrated implementations, portions of the actuation members of the tool driver 502 extending through the sterile barrier 506 are maintained in the sterile field. At the same time, the distal ends of the actuation members of the tool driver 502 that extend distally from the sterile barrier 506 (as shown, e.g., in FIGS. 30 and 31) and engage with corresponding elements of the surgical tool 500 (not shown), are not within the sterile field and should therefore be cleaned before the sterile barrier can be removed after use. FIG. 36 shows an example of a cleaning device 560 that has a plurality of circular brushes (not shown) disposed within housings 562a, 562b, 562c, 562d and configured to be removably disposed over the distal end of the actuation members. Thus, in use, when the cleaning device 560 is disposed over the distal ends of the actuation members, such that each of the housings 562a, 562b, 562c, 562d sits over a corresponding one of the actuation members 504a, 504b, 504c, 504d. The device 560, which can be electrically powered, is activated such that the brushes move (e.g., rotate and/or reciprocate) around the tops of the actuation members and thereby clean the actuation members. The brushes are saturated in a suitable cleaning solution (e.g., disinfectant) that removes and cleans bodily fluids and infectious agents on the tops of the actuation members. The cleaning process using the device 560 can be performed for a suitable duration of time (e.g., about five minutes), after which the device 560 can be removed from the actuation members. The actuation members can be additionally swabbed before the sterile barrier 506 is removed from the tool driver 502.

Figure 37:
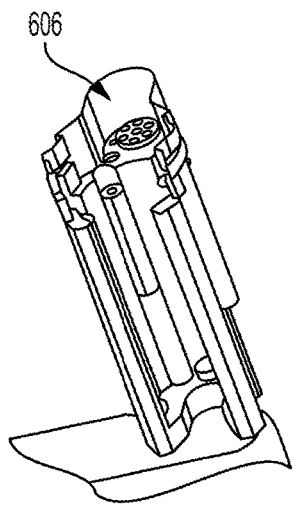
FIG. 37 is a perspective view of one embodiment of a sterile barrier.
Figure 38A:
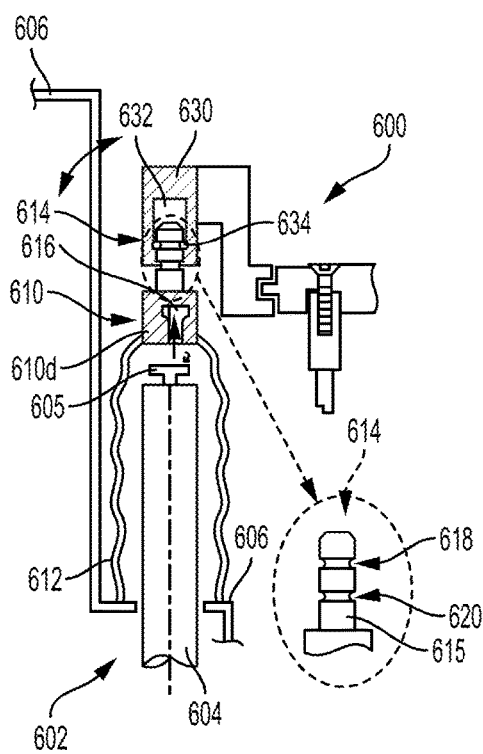
FIG. 38A is a cross-sectional view of another implementation of a proximal portion of a surgical tool and tool driver configured to be coupled via the sterile barrier of FIG. 37.
Figure 38B:
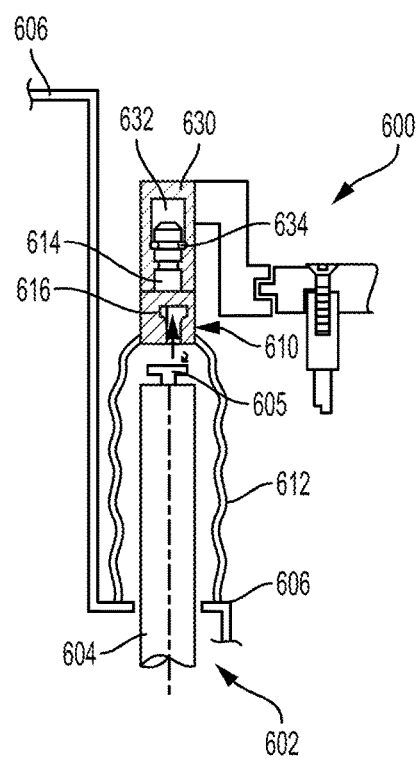
FIG. 38B is another cross-sectional view of the surgical tool, tool driver, and sterile barrier of FIG. 38A.

It should be appreciated that a surgical tool can be coupled to a tool driver through a sterile barrier using various different components. FIGS. 37, 38A, and 38B illustrate an embodiment of a connection between a tool 600 and a tool driver 602 via a sterile barrier 606 intended to prevent contamination of a robotic surgical system during a surgical procedure. The illustrated embodiment provides a low-force connection and disconnection of the tool and the tool driver, which can be performed via a single motion, and with one hand of a user. The self-aligning and intuitive coupling between the tool and the tool driver can thus be achieved.

FIG. 37 illustrates an example of the sterile barrier 606 configured to receive therethrough a plurality (e.g., four or a different number) of actuation members of the tool driver 602. In the illustrated embodiment, each of the actuation members is reversibly coupled to a sterile barrier connector used to couple the actuation member to the surgical tool 600 via the sterile barrier 606. FIGS. 38A and 38B show one actuation member 604 of the tool driver 602 for illustration purposes only, and it should be appreciated that other actuation members of the tool driver 602 can be similarly coupled to the tool 600.

As shown in FIG. 38A, a proximal end 605 of the actuation member 604 is configured to mate with a sterile barrier connector 610 having sterile barrier bellows 612 extending distally therefrom. The distal end of the bellows 612 is sealed and secured to a distal wall 613 of the sterile barrier 606, which allows the actuation member 604 to extend and retract within the bellows 612. In FIGS. 38A and 38B, the sterile barrier connector 610 is shown at a neutral position. The sterile barrier connector 610 and the bellows 612 are configured to be coupled to one another and move proximally and distally (up and down) within the sterile barrier 606.

As shown in FIGS. 38A and 38B, the sterile barrier connector 610 includes a distal portion 610d and a pin 614 disposed proximally of the distal portion 610d and configured to mate with the actuation member 604 of the tool driver 602 and the surgical tool 600, respectively. In particular, the distal portion 610d has a recess 616 formed through a distal end of the sterile barrier connector 610 that is configured to receive the proximal end 605 of the actuation member 604. As shown, in this example the proximal end 605 of the actuation member 604 is a T-shaped element that is configured to be received within the complementary-shaped recess 616 within the distal portion 610d of the sterile barrier connector 610. The pin 614 of the sterile barrier connector 610, additionally shown separately in FIG. 38A, includes a body 615 and first (top or proximal) and second (bottom or distal) grooves 618, 620 that are spaced from one another along the body 615. A connecting member 630 of the surgical tool 600 has a spring 634 (e.g., canted coil spring or other type of spring) disposed within an inner channel 632 thereof. The coil of the spring 634 has an angle that allows it to be locked into the first groove 618 of the pin 614, as discussed below.

In use, the proximal end 605 of the actuation member 604 can be reversibly coupled with the recess 616 in the sterile barrier connector 610 via a T-quarter-turn connection. It should be appreciated, however, that the distal end of the actuation member 604 can have other configurations such that the sterile barrier connector 610 can have an otherwise configured complementary recess. In this example, when the sterile barrier 606 is disposed over the tool driver 602, the actuation member 604 is rotated 90 degrees in one direction such that its proximal end 605 becomes locked with the sterile barrier connector 610. In a similar manner, a rotation in a reverse direction can later be used to disconnect the actuation member 604 from the sterile barrier 606.

In the working position, when the actuation member 604 is engaged with the sterile barrier 606 (which is not shown in FIG. 38A for clarity of illustration), the actuation member 604 is coupled to the sterile barrier 606 such that the connecting member 630 of the surgical tool 600 can only access the first groove 618 of the pin 614 of the sterile barrier connector 610. In other words, only the first groove 618 is available for engagement with the spring 634 disposed in the inner channel 632 of the connecting member 630. As mentioned above, the spring 634 has an angle such that it can be used to lock into the first groove 618. The spring 634 is configured such that it is not able to be uncoupled from the pin 614 until the spring 634 is moved into the second groove 620. In this way, the tool 600 is coupled with the tool driver 602 via the sterile barrier connector 610, as shown in FIG. 38A. The spring-based connection allows the actuation member 604, the sterile barrier connector 610, and the tool's connecting member 630 to move together during a surgical procedure.

After the surgical procedure is completed, the proximal end 605 of the actuation member 604 can be extended proximally (e.g., by a small distance) so as to cause the second groove 620 of the pin 614 become available. As a result, the spring 634 of the tool's connecting member 630 moves from the first groove 618 into the second groove 620 (as shown in FIG. 38B) such that the spring's angle is changed, which reduces significantly force required to uncouple the connecting member 630 from the sterile barrier connector 610. This allows a removal of the connecting member 630 from the sterile barrier connector 610, which can be done with user's one hand.

In some embodiments, a sterile barrier connector (e.g., sterile barrier connector 610 in FIGS. 38A and 38B, or a sterile barrier connector having another configuration) is used and is configured to couple a surgical tool and a tool driver to a sterile barrier disposed between the tool and the tool driver. In some implementations, sterile barrier connectors can be delivered to respective actuation members of a tool driver via a retainer member. The retainer member can be similar to, e.g., removable coupling member 440 (e.g., FIG. 24A), though it can have any other configuration.

Figure 39:
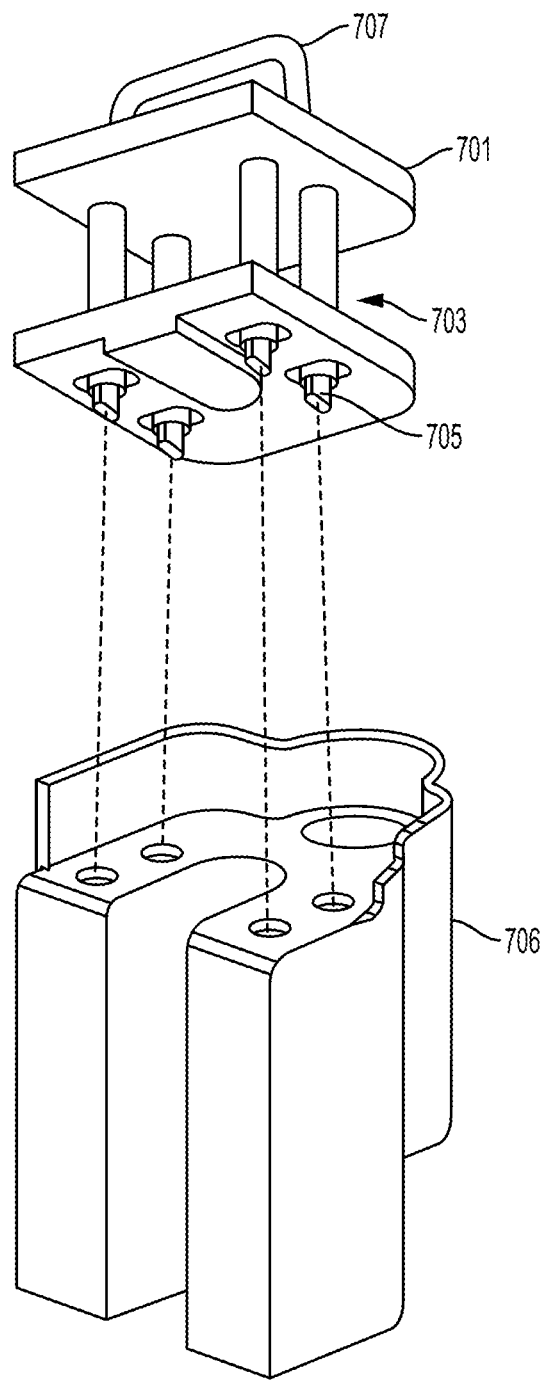
FIG. 39 is a perspective view of one implementation a sterile barrier and a retainer member configured to deliver sterile barrier couplers of the sterile barrier to a tool driver.

FIG. 39 illustrates an example of a retainer member 701 configured to deliver sterile barrier couplers (not shown) to a sterile barrier 706. As shown, the retainer member 701 has a body 703 and a plurality of retainer features 705 configured to engage respective proximal features of the sterile barrier couplers. In this example, four retainer features 705 are shown, though it should be appreciated that the retainer member 701 can include any suitable number of retainer features 705. The retainer member 701 can be operated, e.g., using a handle 707 or other feature(s) to maintain initial positions of the sterile barrier couplers until the actuation members of the tool driver are engaged therewith. Once the actuation members engage distal portions of sterile barrier couplers, the actuation members can be rotated (e.g., 90 degrees) to thus be locked onto the sterile barrier couplers. The retainer member 701 can then be removed and a surgical tool can be loaded into the sterile barrier. Suitable features (e.g., movable portions or plungers) of the surgical tools can then be caused to engage with the sterile barrier couplers that are, in turn, engaged with the tool driver's actuation members.

FIGS. 40A-40E illustrate schematically an example of a method of using a retainer member 801, such as the retainer member 701 (FIG. 39), to reversibly mate a proximal end 805 of an actuation member 804 of a tool driver (not shown) with a sterile barrier coupler 808. As a person skilled in the art will appreciate, other actuation members of the tool driver can be configured to mate with respective sterile barrier couplers in a similar manner. Moreover, as discussed above, the retainer member 801 is configured to simultaneously deliver sterile barrier couplers to all actuation members of the tool driver. Similarly, the sterile barrier couplers can be simultaneously removed from the actuation members using the retainer member 801.

Figure 40:
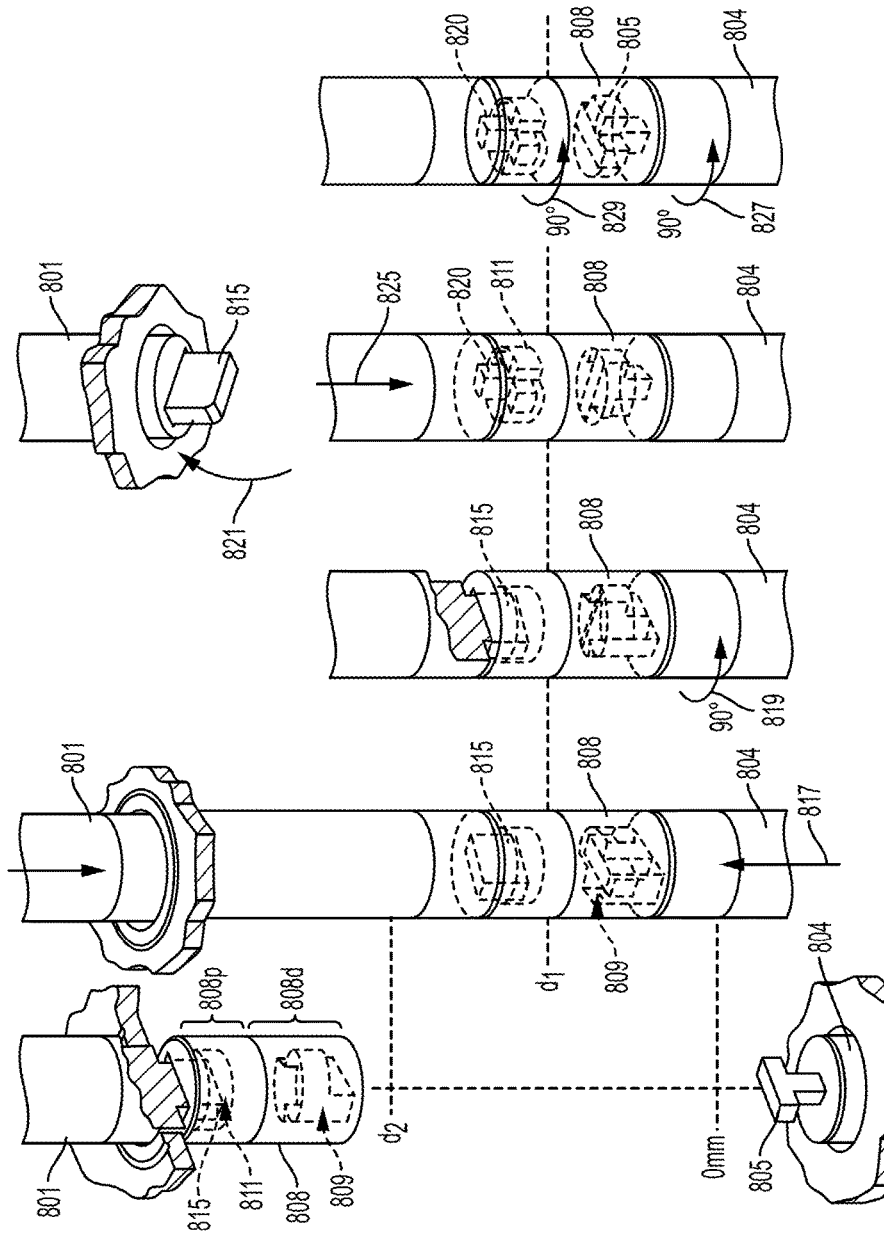
FIGS. 40A-40E are schematic diagrams illustrating a method of using a retainer member to deliver a sterile barrier coupler to a tool driver and of coupling a surgical tool to the sterile barrier coupler.

As shown in FIG. 40A, the sterile barrier coupler 808 has a first or distal portion 808d having a first or distal recess 809 configured to engage with, in this example, T-shaped proximal end 805 of the actuation member 804. The sterile barrier coupler 808 also has a second or proximal portion 808p having a second or proximal recess 811 configured to engage a complementary-shaped retainer feature 815 of the retainer member 801. In use, as shown in FIG. 40A, the retainer member 801 is used to deliver the sterile barrier coupler 808 to the actuation member 804 that is shown separately. Also, in FIG. 40A, the distal end of the sterile barrier coupler 808 is shown at a distance d2 (e.g., greater than about 30 mm) from the proximal end 805 of the actuation member 804. In FIGS. 40B-40E, the distance d1 is about 15 mm.

As shown in FIG. 40B, the proximal end 805 of the actuation member 804 is advanced distally into the distal recess 809 in the sterile barrier coupler 808, as shown by arrow 817. At this point, the retainer member 801 maintains the initial position of the sterile barrier coupler 808. Once the actuation member 804 engages the distal recess 809 of the sterile barrier coupler 808, the actuation member 804 can be rotated (e.g., 90 degrees), as shown by arrow 819 in FIG. 40C, to thus be locked onto the sterile barrier coupler 808. The retainer member 801 can then be removed from the sterile barrier coupler 808 (and from all other sterile barrier couplers), as shown schematically by arrow 821 in FIG. 40D. A suitable feature of a surgical tool (not shown) can then be coupled to the actuation member 804 via the sterile barrier coupler 808. The sterile barrier coupler 808 can be disposed within a sterile barrier of any suitable configuration.

After the retainer member 801 is removed, a distal end 820 of a suitable actuation member of the surgical tool (e.g., an input rod or other feature, not shown) can be advanced into engagement with the sterile barrier coupler 808, as shown by arrow 825 in FIG. 40D, so as to become reversibly mated with the proximal recess 811 formed in the sterile barrier coupler 808, as also shown schematically in FIG. 40D. A second rotation (e.g., 90 degrees), as shown by arrows 827, 829 in FIG. 40E, of the actuation member 804 and sterile barrier coupler 808 coupled to each other, causes a T-shaped distal end 820 of the actuation member of the surgical tool to mate with the proximal recess 811 of the sterile barrier coupler 808, thus allowing the tool actuation member (only the distal end 820 of which is shown) to be coupled thereto to move proximally and distally by a distance (e.g., of about 30 mm) within the sterile barrier.

In some embodiments, a retainer member may not be used. FIGS. 41 and 42A-42D illustrate another embodiment of a sterile barrier coupler 908 of a sterile barrier 906 configured to couple a surgical tool 900 to a tool driver 902 through the sterile barrier. As shown schematically in FIG. 41, the sterile barrier coupler 908, having an elastomeric bellows 912 extending distally therefrom, is configured to couple with a proximal end 905 of an actuation member 904 of the tool driver such that the sterile barrier coupler 908 and the actuation member 904 coupled thereto can move proximally and distally by a distance of about 30 mm. It should be appreciated that one actuation member 904 is shown by way of example only, as the tool driver 902 has four similar actuation members. Alternatively, in some implementations, the tool driver 902 can have a different number of actuation members (e.g., less than four or greater than four).

Figure 41:
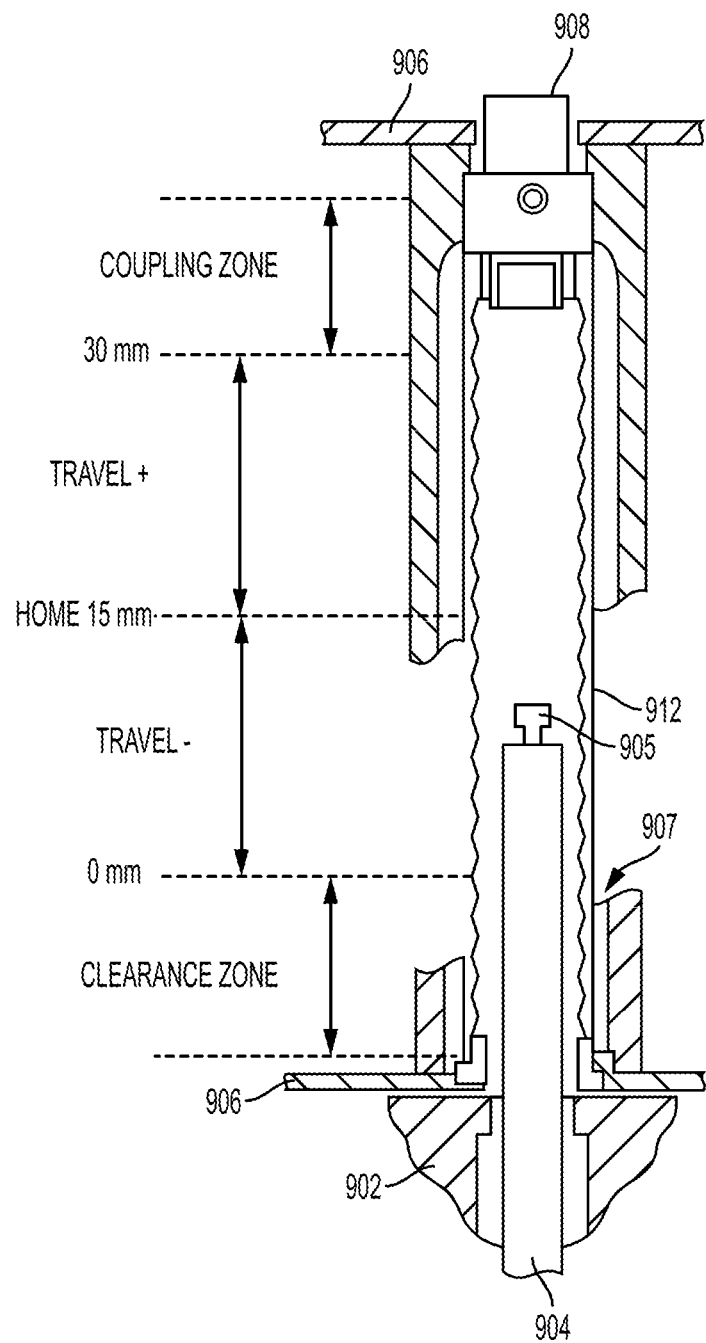
FIG. 41 is a cross-sectional view of one implementation of a sterile barrier coupler configured to couple an actuation member and a surgical tool to one another via a sterile barrier.

FIG. 41 further illustrates that the sterile barrier 906 is configured to allow for a clearance zone encompassing at least a portion of the actuation member 904 and a coupling zone encompassing at least a portion of the sterile barrier coupler 908. As shown in FIG. 41, in this example, the actuation member 904 can move from the "home" position (15 mm) distally ("Travel –") to a distal-most position (0 mm) and proximally ("Travel +") to a proximal-most position (30 mm). It should be appreciated that the distance of from about 0 mm to about 30 mm by which the actuation member 904 can move within the sterile barrier is shown by way example only.

In the illustrated implementation, the sterile barrier bellows 912 with the sterile barrier coupler 908 moves proximally and distally (up and down) in a circular pocket or channel 907 of the sterile barrier 906. The channel 907 allows rotational or linear translation of the sterile barrier coupler 908 within the sterile barrier 906. The channel 907 has, at the most proximal end thereof, a curved path 911 formed in the walls of the sterile barrier 906 (e.g., in the housing of the sterile barrier 906 having a suitable configuration). The path 911 causes the sterile barrier coupler 908 to rotate as the sterile barrier coupler 908 travels distally while making a connection between the surgical tool 900 and the tool driver 902.

Figure 42:
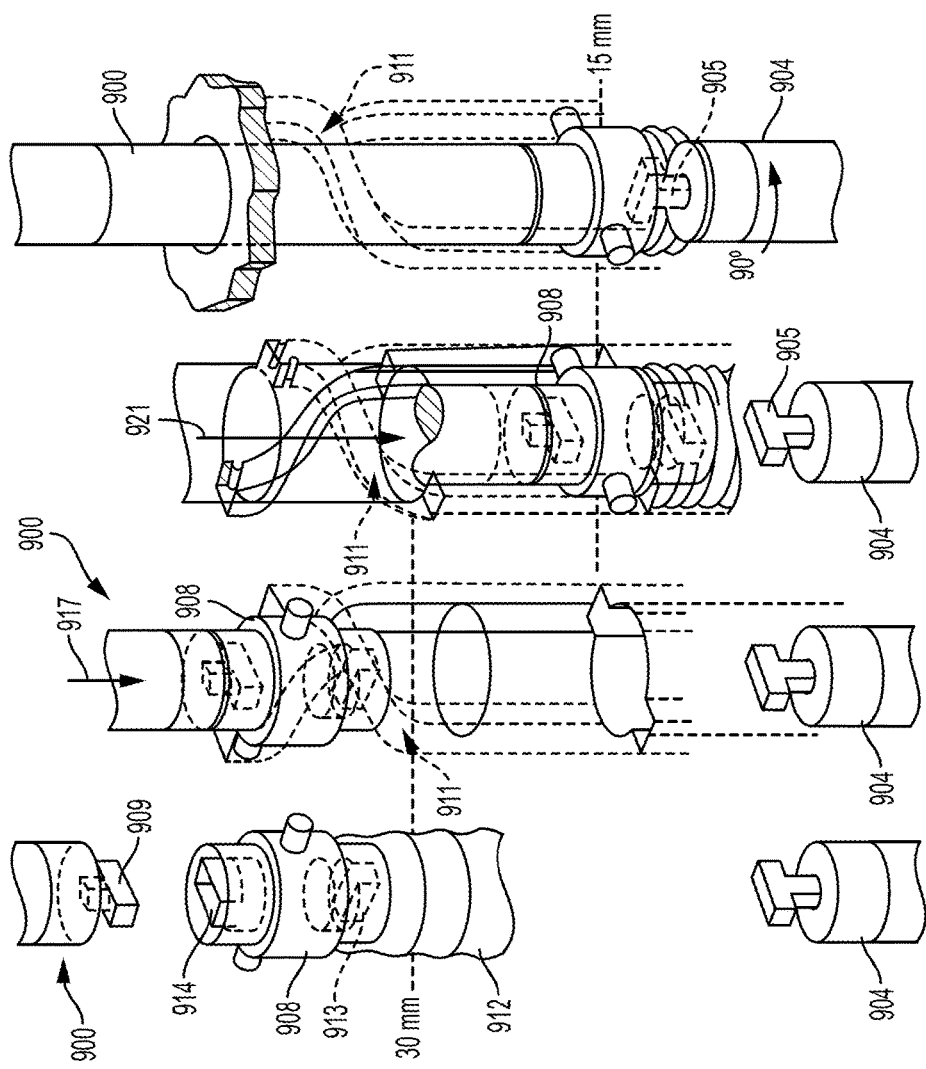
FIGS. 42A-42D are schematic diagrams illustrating a method of using the sterile barrier coupler of FIG. 41 to couple the actuation member and the surgical tool.

FIG. 42A shows a distal end 909 (T-shaped, in this example) of the surgical tool 900 that is configured to engage a complementary-shaped proximal recess 914 in the sterile barrier coupler 908. The sterile barrier coupler 908 also has a distal recess 913 configured to receive therein the proximal end 905 of the actuation member 904. FIG. 42B shows the distal end 909 of the tool 900 advanced distally, as shown by arrow 917, to mate with the recess 914 in the sterile barrier coupler 908. As the surgical tool 900 is advanced distally (921) into the sterile barrier 906, the sterile barrier coupler 908 is also moved distally as the path 911 in the sterile barrier walls causes the sterile barrier coupler 908 to rotate 90 degrees, as shown in FIG. 42C. In this way, the sterile barrier coupler 908 reaches the actuation member 904 and makes a connection therewith, such that the distal recess 913 of the sterile barrier coupler 908 receives therein the proximal end 905 of the actuation member 904, as shown schematically in FIG. 42D. As also shown in FIG. 42D, the actuation member 904 is advanced proximally and rotated 90 degrees to complete the coupling between the actuation member 904 and the surgical tool 900 through the sterile barrier 906 using the sterile barrier coupler 908. This sequence of operations can be reversed to decouple the surgical tool 900 from the actuation member 904.

The embodiment illustrated in FIGS. 41 and 42A-42D provides a straightforward connection and disconnection of the tool and the tool driver, which can be done via a single motion, using one hand of a user. The self-aligning and intuitive coupling between the tool and the tool driver can thus be achieved.

In some embodiments, features other than sterile barrier couplers can be used to reversibly couple a surgical tool to a tool driver via a sterile barrier. Regardless of the specific configuration of such feature(s), they should facilitate multiple translating (push/pull) connections and must be easily attachable/removable with little alignment or rotational sensitivity. Accordingly, in some embodiments, a push/pull connection between a surgical tool and a tool driver can be implemented using a colleted mechanism. As shown schematically in FIG. 43, a connector 1008 includes first and second recesses 1003, 1005 that are configured to seat therein collet members 1012, 1014, respectively. The collet member 1012 has flanges 1016 and the collet member 1014 has flanges 1018, as shown in FIG. 43.

When an actuation member is inserted into a recess in the connector 1008, the side of the collet disposed in that recess that is opposite to the flange expands. When the actuation member is retracted for the pulling motion, the expanded collet rides down and interferes with the interior walls of the recess in the connector, thus preventing removal of the actuation member. At the same time, if the flange on the collet is pushed into the connector, a clearance fit allows the collet to expand. Thus, if the collet is pressed in while the actuation member is retracted simultaneously, a decoupling can occur.

Figure 43:
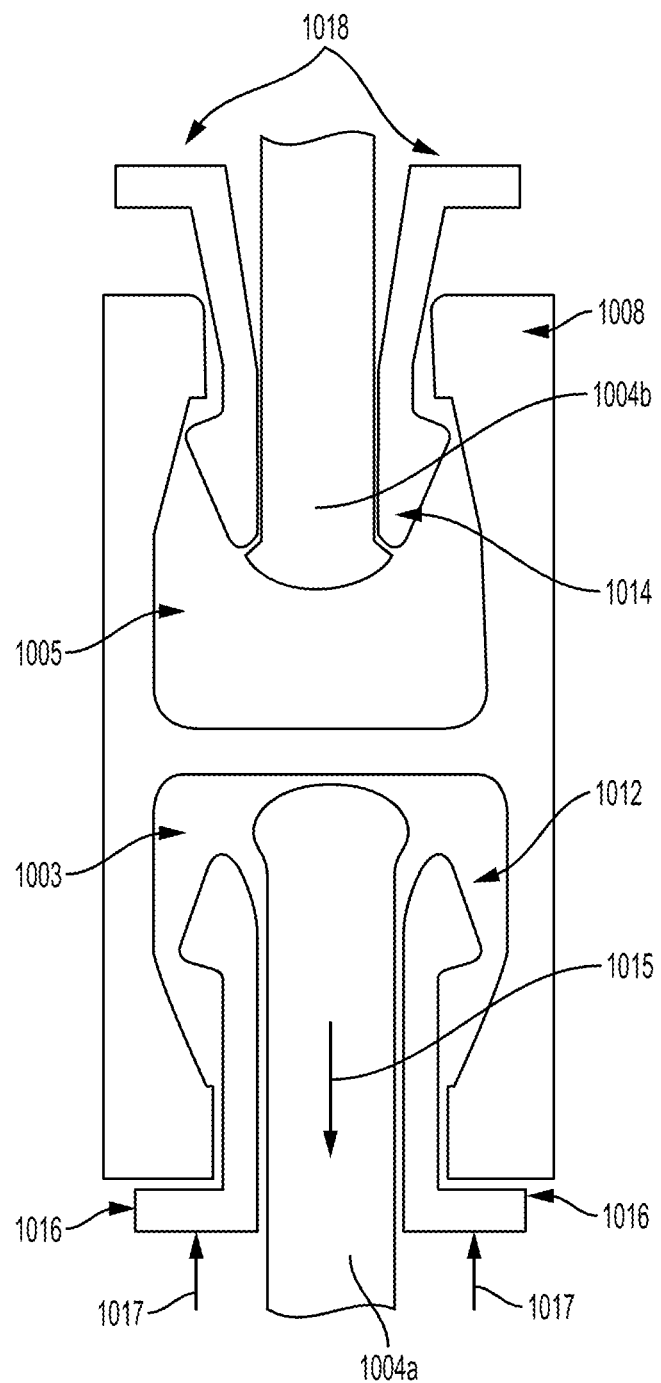
FIG. 43 is a schematic cross-sectional view of one implementation of a collet member in accordance with the described techniques.

FIG. 43 illustrates that the connector 1008 can receive ends of elongate members 1004a, 1004b in the first and second recesses 1003, 1005 seating the collet members 1012, 1014. The recess 1003 is shown by way of example only to receive the member 1004a in a "push" state, as also shown schematically by arrow 1015. To remove the member 1004a, load should be applied into the flanges 1016, as shown by arrows 1017. The recess 1005 is shown by way of example only to receive the member 1004b in a retracted or "pull" state.

It should be appreciated that one of the members 1004a, 1004b can be an actuation member of a tool driver, and another one of the members 1012, 1014 can be an actuation element of a surgical tool. In this way, as in the example illustrated, the connector 1008 can be configured to have symmetrical recesses seating therein similar or identical collet members, such that one side of the connector 1008 is coupled to the tool driver and another side of the connector is coupled to the tool. In other embodiments, one type of a collet member can be used to reversibly couple with an actuation member of a tool driver, and another, different type of a collet member can be used to reversibly couple with an actuation feature of a surgical tool.

It should be appreciated that the collet members 1012, 1014 are shown in FIG. 43 by way of example only, and that they can have any other suitable configuration. For example, their end features disposed in the recess can be mushroom-shaped, ball-shaped, or shaped in any other manner. A back surface for the collet to collapse or contract can be configured to provide additional opposing surface to load against for tension/retraction positions. Furthermore, the connector 1008 can be disposed at any suitable location within a sterile barrier. For example, it can be disposed in proximity to a ledge or face (e.g., the proximal end) in the sterile barrier, or disposed in another suitable location. Regardless of the specific configuration and type of the collet mechanism, the described embodiments provide a connection that does not require rotation of the sterile barrier components, and coupling/decoupling can be accomplished with using simplified elements.

FIG. 44 illustrates another embodiment of a coupling mechanism configured to reversibly couple a surgical tool to a tool driver via a sterile barrier. In this embodiment, a push/pull collet member 1110 on an actuation member of a tool driver (not shown) is coupled to an actuation feature such as an input rod 1120 of a surgical tool 1100 via an H-shaped connecting clip member 1108 having a sterile barrier bellows 1112 extending therefrom. The clip member 1108 includes a first clip portion 1108a, a living hinge 1109, and a second clip portion 1108b. When a sterile barrier 1106 is installed, the clip member 1108 is disposed adjacent to, but not connected to the collet member 1110. When the surgical tool 1100 is inserted into the sterile barrier 1106, the input rod 1120 is inserted inside of, but is not connected to, the clip member 1108.

In the illustrated embodiments, the tool driver is configured to be connected to the input rod 1120 via the clip member 1108. The clip member 1108 includes a pin 1116 extending through an outer tube 1118 of the collet member 1110 and configured to translate to expand the collet member 1110. By expanding the outer tube 1118 of the collet member 1110, the first clip portion 1108a of the clip member 1108 is caused to open (i.e. its arms open) and thereby engage with the collet member 1110. When the arms of the first clip portion 1108a are caused to open, the arms of the second clip portion 1108b are caused to come together to thus close. When the second clip portion 1108b is in the closed configuration, the clip member 1108 becomes connected to the input rode 1120. At this point, translation (e.g., pushing and pulling) of the collet member 1110 directly causes the input rod 1120 to be pushed and pulled.

The embodiment described in FIG. 44 provides the connection between the tool and the tool driver that does not require rotation of the sterile barrier components. Also, actuation can be performed using only components of the tool driver. In addition, coupling/decoupling can be performed regardless of the positions of the actuation members of the tool driver.

As mentioned above, sterile barrier couplers and other coupling components configured to reversibly couple a surgical tool and a tool driver via a sterile barrier can have a number of different configurations. FIGS. 45A, 45B, 46A, and 46B illustrate another embodiment of a sterile barrier coupler 1208 configured to reversibly couple a surgical tool 1200 and a tool driver 1202 via a sterile barrier 1206. In this implementation, the sterile barrier 1206 includes a helical coupling mechanism including a helical track 1210 and a compression spring 1214. The helical track 1210 can be formed in the walls of the sterile barrier 1206 (e.g., in the housing of the sterile barrier 1206 having a suitable configuration). The sterile barrier 1206 also includes a guide pin 1216 shown in FIG. 45A. The sterile barrier coupler 1208 has a bellows 1212 coupled thereto and extending distally therefrom.

As shown in more detail in FIG. 45B, the sterile barrier coupler 1208 has a window or opening 1218 configured to receive therein a distal end 1220d of the tool actuation member 1220. The opening 1218 can have features that facilitate a reversible mating between the sterile barrier coupler 1208 and the tool actuation member 1220. For example, the inner walls of the opening 1218 can have an undercut feature 1225 configured to receive therein a coupling feature 1222 formed at the distal end 1220d of the tool actuation member 1220, as shown in FIGS. 45A and 45B. In this example, the coupling feature 1222 is in the form of a semi-circular protrusion extending from an elongate cylindrical body 1223 of the tool actuation member 1220, though it can have other configurations.

As shown in FIGS. 45A, 45B, 46A, and 46B, similar to the other embodiments described herein, the tool driver 1202 has a plurality of actuation members, one of which, an actuation member 1204 configured to mate with the sterile barrier coupler 1208, is shown in FIGS. 45A, 45B, 46A, and 46B by way of example only. For example, the tool driver 1202 can include four actuation members configured to mate with respective four sterile barrier couplers that are similar to the sterile barrier coupler 1208. A distal end of the bellows 1212 can be sealed and secured to a distal wall of the sterile barrier 1206 (e.g., similar to the techniques as shown in FIG.

34, or in any other suitable way), which allows the actuation member 1204 to extend and retract within the bellows 1212. The sterile barrier coupler 1208 and the bellows 1212 coupled thereto move proximally and distally (up and down) inside the sterile barrier 1206.

Figure 46A:
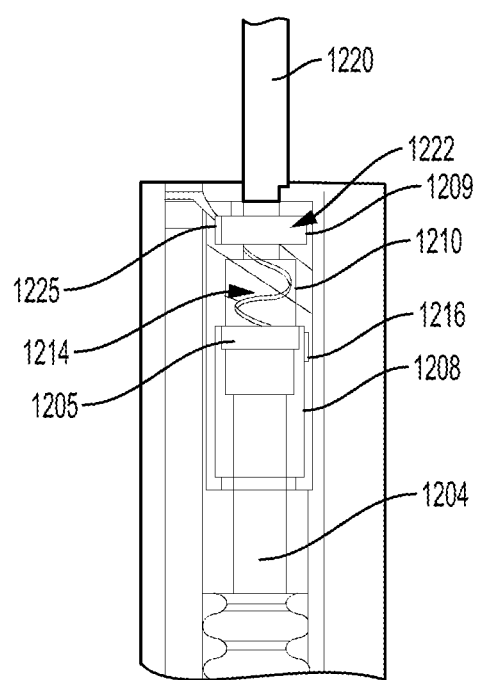
FIG. 46A is a cross-sectional view of the sterile barrier coupler, the actuation member, and the surgical tool of FIG. 45A, showing the surgical tool being coupled to the sterile barrier coupler.

Each of the actuation members is configured to reversibly mate with a respective sterile barrier coupler. Thus, the actuation member 1204 is shown mated with the sterile barrier coupler 1208, which can be done in any suitable ways. For example, as shown in FIGS. 45A and 46A, a proximal end 1205 of the actuation member 1204 can be received (e.g., fittingly) with the distal portion of the sterile barrier coupler 1208, which can have features that facilitate the reversible mating between the sterile barrier coupler 1208 and the actuation member 1204. The sterile barrier couplers are disposed around a perimeter of an outer wall of a mating interface member (not shown) of the surgical tool 1200 (e.g., similar to the implementation shown in FIG. 7). Initially, the sterile barrier couplers are positioned at a neutral position and are not coupled to actuation member of the tool driver.

FIGS. 45A and 45B show the components of this embodiment in a position in which the tool 1200 is not coupled to the tool driver 1202. Before the coupling process is completed, the actuation members of the tool driver 1202 can all be positioned at the same height within the tool driver 1202, which is a so-called alignment position. Each of the actuation members has a respective sterile barrier coupler attached thereto, with the spring (e.g., spring 1214) disposed between the proximal-most end of each actuation member and the sterile barrier coupler. The spring compresses as the sterile barrier coupler moves distally.

Figure 46B:
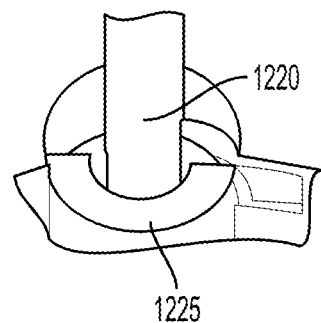
FIG. 46B is an enlarged view of the sterile barrier coupler and a distal portion of a tool actuation member of the surgical tool of FIG. 46A.

In the illustrated implementation, the surgical tool 1200 can be attached to the tool driver 1202 by first advancing a tool actuation member 1220 (e.g., input rod or other component configured to couple with the corresponding tool driver's actuation member) distally into the sterile barrier coupler 1208 of the sterile barrier 1206. At that point, the tool actuation member 1220 (and thus the tool 1200) is not coupled to the tool driver 1202. As the tool actuation member 1220 pushes down on the sterile barrier coupler 1208, the sterile barrier coupler 1208 is caused to rotate along the helical track 1210 in the sterile barrier 1206. During the rotation of the sterile barrier coupler 1208, the coupling feature 1222 of the tool actuation member 1220 slides underneath the undercut 1225 formed in the opening 1218 of the sterile barrier coupler 1208, thereby coupling the tool actuation member 1220 and the sterile barrier coupler 1208, as shown in FIGS. 46A and 46B, illustrating the components of this embodiment in a position in which the tool 1200 is coupled to the tool driver 1202.

The tool actuation member 1220 is advanced distally until it abuts against a stop surface 1209 in the sterile barrier, as shown in FIG. 46A. During such distal movement of the tool actuation member 1220, the helical track 1210 in the sterile barrier 1206 causes the sterile barrier coupler 1208 to couple the tool actuation member 1220 and the actuation member 1204, driving approximately the last ¼ of the stroke. As shown in FIG. 46A, when the tool actuation member 1220 is coupled to the actuation member 1204, the guide pin 1216 pushes against the proximal end 1205 of the actuation member 1204, thereby retaining the actuation member 1204 within the sterile barrier coupler 1208.

The embodiment illustrated in FIGS. 45A, 45B, 46A, and 46B provides a straightforward connection and disconnection of the tool and the tool driver, which can be done via a single motion, using one hand of a user. The self-aligning and intuitive coupling between the tool and the tool driver can thus be achieved. Once the tool actuation member 1220 is coupled to the actuation member 1204 via the sterile barrier coupler 1208 (and thus via the sterile barrier coupler 1206), the tool driver 1202 can move the actuation member 1204 (as well as other actuation members not shown for the sake of simplicity) away from the alignment position, thus allowing for push and pulled movements at the interface between the tool actuation member 1220 and the actuation member 1204.

Preferably, components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A robotic surgical tool comprising:
   a housing comprising a mating interface member having a plurality of independently movable portions;
   an elongate shaft extending distally from the housing;
   an end effector coupled to a distal end of the elongate shaft; and
   a plurality of coupling features disposed about a perimeter of an outer wall of the mating interface member, each of the plurality of coupling features being coupled to a movable portion and being configured to reversibly engage with a proximal end of a corresponding actuation member from a plurality of actuation members of a tool driver;
   wherein the coupling features are configured to reversibly engage with the proximal ends of the actuation members so as to allow the actuation members to move in proximal and distal directions independently from one another to thereby control operation of the end effector.

2. The robotic surgical tool of claim 1, further comprising a sterile barrier configured to be disposed between the surgical tool and the tool driver so as to define a sterile side at which the surgical tool is disposed and a non-sterile side at which a portion of the tool driver is disposed, the sterile barrier encompassing the coupling features engaged with the proximal ends of the actuation members.

3. The robotic surgical tool of claim 1, wherein each coupling feature has an opening extending longitudinally therethrough that is configured to receive at least a portion of the proximal end of the actuation member.

4. The robotic surgical tool of claim 1, wherein each coupling feature has an inner channel, an annular groove extending around at least a portion of an outer wall of the coupling feature, and a spring disposed around the outer wall and configured to engage a circumferential groove in the proximal end of the actuation member exposed through the annular groove when the proximal end is received within the inner channel of the coupling feature.

5. The robotic surgical tool of claim 4, wherein the tool includes a movable disengagement member configured to cause all of the plurality of actuation members to simultaneously disengage from the coupling features.

6. The robotic surgical tool of claim 5, wherein the disengagement member is a generally cylindrical member having an open-ended passage extending therethrough and comprising first and second opposed ends connected by a plurality of longitudinal struts.

7. The robotic surgical tool of claim 6, wherein the disengagement member is disposed around the mating interface member that extends through the open-ended passage.

8. The robotic surgical tool of claim 6, wherein the disengagement member is configured to be rotated about its longitudinal axis so as to cause each longitudinal strut to move and to thereby disengage a respective spring from the circumferential groove in the proximal end.

9. The robotic surgical tool of claim 1, wherein each coupling feature is coupled to the proximal end of the actuation member via a sterile barrier coupler from a plurality of sterile barrier couplers, the sterile barrier coupler having a proximal portion configured to engage the coupling feature and a distal portion configured to engage the proximal end of the actuation member.

10. The robotic surgical tool of claim 9, wherein the proximal portion of the sterile barrier coupler comprises a first recess configured to engage the coupling feature and the distal portion of the sterile barrier coupler comprises a second recess having a shape complementary to a shape of the proximal end of the actuation member.

11. The robotic surgical tool of claim 9, wherein the sterile barrier includes a removable coupling member configured to removably engage with the sterile barrier couplers and configured to be operated to simultaneously reversibly mate the sterile barrier couplers with the proximal ends of the actuation members.

12. The robotic surgical tool of claim 11, wherein the removable coupling member comprises an actuator, a body, and a plurality of coupling sleeves extending from the body and configured to reversibly engage with the sterile barrier couplers, wherein the actuator is configured to be rotated in a first direction to cause the sleeves to rotate and thereby cause the sterile barrier couplers engaged with the sleeves to engage with the proximal ends of the actuation members, and in a second, opposite direction to cause the sleeves to rotate and thereby cause the sterile barrier couplers engaged with the sleeves to disengage from the proximal ends of the actuation members.

13. The robotic surgical tool of claim 9, further comprising a rotatable portion disposed proximally of the elongate shaft and configured to be axially rotated between a first position and a second position to thereby cause all of the coupling features to simultaneously engage with and simultaneously disengage from corresponding proximal portions of the sterile barrier couplers.

14. The robotic surgical tool of claim 9, wherein:
the distal portion of each of the sterile barrier couplers has a bellows extending distally therefrom,
a proximal portion of the actuation member having its proximal end engaged with the distal portion of the sterile barrier coupler extends through the bellows; and
a distal end of the bellows is disposed at a distal end of the sterile barrier.

15. The robotic surgical tool of claim 14, wherein each of the bellows allows the proximal portion of the actuation member extending therethrough to move therewithin in proximal and distal directions such that the actuation members move independently from one another.

16. The robotic surgical tool of claim 1, wherein each actuation member is operably coupled with at least one motor disposed in the tool driver and configured to control movement of the actuation member.

* * * * *